(12) United States Patent
Dutta et al.

(10) Patent No.: US 11,583,578 B2
(45) Date of Patent: Feb. 21, 2023

(54) PLASMODIUM FALCIPARUM RECOMBINANR XIEXUMAPOEOZOITE PROTEIN COMPOSITIONS AND METHOD FOR VACCINE DELIVERY

(71) Applicants: The Henry M. Jackson Foundation for the Advancement of Military Medicine, Inc., Bethesda, MD (US); The Government Of The United States, As Represented By The Secretary Of The Army, Fort Detrick, MD (US)

(72) Inventors: Sheetij Dutta, Silver Spring, MD (US); Zoltan Beck, Rockville, MD (US); Carl Alving, Bethesda, MD (US); Gary Matyas, Olney, MD (US)

(73) Assignees: The Henry M. Jackson Foundation for the Advancement of Military Medicine, Inc., Bethesda, MD (US); The Government Of The United States, As Represented By The Secretary Of The Army, Fort Detrick, MD (US)

(*) Notice: Subject to any disclaimer, the term of this patent is extended or adjusted under 35 U.S.C. 154(b) by 441 days.

(21) Appl. No.: 16/607,917

(22) PCT Filed: Apr. 27, 2018

(86) PCT No.: PCT/US2018/029906
§ 371 (c)(1),
(2) Date: Oct. 24, 2019

(87) PCT Pub. No.: WO2018/201022
PCT Pub. Date: Nov. 1, 2018

(65) Prior Publication Data
US 2022/0160855 A1    May 26, 2022

Related U.S. Application Data

(60) Provisional application No. 62/491,463, filed on Apr. 28, 2017.

(51) Int. Cl.
*A61K 39/015*    (2006.01)
*A61K 39/39*    (2006.01)
*A61K 39/00*    (2006.01)

(52) U.S. Cl.
CPC .......... *A61K 39/015* (2013.01); *A61K 39/39* (2013.01); *A61K 2039/545* (2013.01);
(Continued)

(58) Field of Classification Search
CPC ........ A61K 39/015; A61K 2039/55555; A61K 2039/55577; A61P 33/06
See application file for complete search history.

(56) References Cited

U.S. PATENT DOCUMENTS 6,007,838 A   12/1999 Alving et al.
7,147,862 B1   12/2006 Prieels et al.
(Continued)

FOREIGN PATENT DOCUMENTS

ES       2445170       2/2014
WO    WO2008086386 A2 *  7/2008
(Continued)

OTHER PUBLICATIONS

Genito et al., Liposomes Containing Monophosphoryl Lipid A and QS-1 Serve as Effective Adjuvant for Soluble Circumsporozite Protein Malaria Vaccine FMP013, Vacccine 35, pp. 3865-3874 (Year: 2017).*
(Continued)

*Primary Examiner* — Carlos A Azpuru
(74) *Attorney, Agent, or Firm* — McNeill Baur, PLLC

(57) ABSTRACT

The invention relates to pharmaceutical compositions comprising at least one antigen and an adjuvant composition,
(Continued)

where the adjuvant composition comprises a saponin and a liposome. The liposome of the composition comprises monophosphoryl lipid A (MPLA), cholesterol and a phospholipid that is in a liquid crystalline state at greater than or equal to 23° C., and the concentration of cholesterol to lipid in the liposome is greater than 50% (mol/mol). The antigen in the composition is a soluble *Plasmodium falciparum* recombinant circumsporozoite protein (rCSP) comprising the amino acid sequence of SEQ ID NO:1, or a *P. falciparum* rCSP peptide that is at least 95% identical to the amino acid sequence of SEQ ID NO:1.

25 Claims, 16 Drawing Sheets

Specification includes a Sequence Listing.

(52) U.S. Cl.
CPC .............. *A61K 2039/55555* (2013.01); *A61K 2039/55572* (2013.01); *A61K 2039/55577* (2013.01)

(56) References Cited

U.S. PATENT DOCUMENTS

| 2014/0341974 | A1 | 11/2014 | Sorayya et al. | |
|---|---|---|---|---|
| 2016/0038580 | A1* | 2/2016 | Dutta | C07K 14/445 424/191.1 |
| 2016/0228573 | A1 | 8/2016 | Niyikiza et al. | |

FOREIGN PATENT DOCUMENTS

| WO | 2014171116 A1 | 10/2014 |
|---|---|---|
| WO | 2015148648 A1 | 10/2015 |

OTHER PUBLICATIONS

Beck et al., "Differential immune responses to HIV-1 envelope protein induced by liposmal adjuvant formulations containing monophosphoryl lipid A with or without QS21," Vaccine, vol. 33, No. 42, pp. 5578-5587 (Sep. 13, 2015) (10 pages).

Genito et al., "Plasmodium falciparum circumsporozoite protein adjuvanted with liposmal adjuvant induces highly protective responses in C57BL/6 mice against transgenic parasite challenge," American Journal of Tropical Medicine and Hygiene, vol. 95, No. 5, Supplement 1, pp. 514-515 (Nov. 1, 2016) (2 pages).

Extended European Search Report issued in corresponding European Application No. 18791678.8, dated Feb. 8, 2021.

Beck et al., "Detection of liposomal cholesterol and monophosphoryl lipid A by QS-21 saponin and Limulus polyphemus amebocyte lysate," Biochimica et Biophysica Acta 1848: 775-780 (2015).

Genito et al., "Liposomes containing monophosphoryl lipid A and QS-21 serve as an effective adjuvant for soluble circumsporozoite protein malaria vaccine FMP013," Vaccine 35: 3865-3874 (2017).

International Search Report issued in corresponding International Patent Application No. PCT/US2018/029906 dated Aug. 29, 2018.

Written Opinion issued in corresponding International Patent Application No. PCT/US2018/029906 dated Aug. 29, 2018.

* cited by examiner

PLASMODIUM FALCIPARUM RECOMBINANR XIEXUMAPOEOZOITE PROTEIN COMPOSITIONS AND METHOD FOR VACCINE DELIVERY

STATEMENT REGARDING FEDERALLY SPONSORED RESEARCH OR DEVELOPMENT

This invention was made with government support under W81XWH-11-2-0174 awarded by the United States Army Medical Research and Materiel Command. The government has certain rights in this invention.

SEQUENCE LISTING SUBMISSION VIA EFS-WEB

A computer readable text file, entitled "SequenceListing.txt," created on or about Oct. 24, 2019 with a file size of about 21 kb contains the sequence listing for this application and is hereby incorporated by reference in its entirety.

BACKGROUND OF THE INVENTION

The invention relates to pharmaceutical compositions comprising at least one antigen and an adjuvant composition, where the adjuvant composition comprises a saponin and a liposome. The liposome of the composition comprises monophosphoryl lipid A (MPLA), cholesterol and a phospholipid that is in a liquid crystalline state at greater than or equal to 23° C., and the concentration of cholesterol to lipid in the liposome is greater than 50% (mol/mol). The antigen in the composition is a soluble *Plasmodium falciparum* recombinant circumsporozoite protein (rCSP) comprising the amino acid sequence of SEQ ID NO:1, or a *P. falciparum* rCSP peptide that is at least 95% identical to the amino acid sequence of SEQ ID NO:1.

BACKGROUND OF THE INVENTION

Malaria caused by the *Plasmodium falciparum* parasite kills hundreds of thousands in the poorest regions of the world. Fast spreading multi-drug-resistant strains of this parasite underline the need for a safe and efficacious vaccine. The circumsporozoite protein (CSP) is abundant on the surface of the mosquito-transmissible stage of the parasite called the sporozoite. CSP molecules contain a tetra-peptide (NANP)n repeating unit flanked by conserved amino terminal region (N-term) and a polymorphic, cysteine-rich carboxy-terminal (C-term) region.

Early CSP vaccines were based on recombinant proteins that were either soluble proteins or long synthetic peptides formulated in Alum. These early vaccines showed low levels of inconsistent protection in controlled human malaria infection (CHMI) trials. A significant improvement in efficacy was observed when RTS,S, a particulate CSP based vaccine was tested in combination with a rationally designed molecular adjuvant AS02 (GlaxosmithKline).

AS02 adjuvant contained oil-emulsion and two naturally occurring immune-stimulators: monophosphoryl lipid A (MPLA) derived from bacterial membranes and QS21 extracted from the bark of *Quillaria saponaria* soap tree (Stoute et al. (1997) N Engl J Med 336:86-91). AS02 adjuvant was replaced by AS01 adjuvant in the current generation of RTS,S vaccine. Based on the data from extensive Phase-3 trials in Africa, a pediatric version of RTS,S in AS01E adjuvant has been approved for limited clinical use in three African countries under the trade name Mosquirix® (Takita-Sonoda et al. (1996) Exp. Parasitol. 84:223-230; Regules et al. (2016) J. Infect. Dis. 214:762-771; Kester et al. (2009) J. Infect. Dis. 200:337-346). Mosquirix® is based on the 3D7 strain of *P. falciparum* CSP and it confers sterile protection among a significant portion of the vaccines challenged with a homologous parasite strain in CHMI. Efficacy of Mosquirix® against natural infection however remains low and strategies to augment the duration and spectrum of protection against field isolates continues.

RTS,S contains the central repeat and C-term region of CSP, but this vaccine lacks the N-term region of the CSP molecule. A way to improve efficacy of CSP can be to include the B- and T-cell epitopes as well as a protease cleavage site present in the N-terminal region of CSP (Herrera et al. (2015) Infect. Immun. 83:3771-3780; Bongfen et al. (2009) Vaccine 27:328-335; Coppi et al. (2011) J. Exp. Med. 208:341-356; Tewari et al. (2002) J. Biol. Chem. 277:47613-47618; Espinosa et al. (2015) J. Infect. Dis. 212:1111-1119). WRAIR's *Falciparum* Malaria Vaccine-013 (FMP013) is a formulation that contains a nearly full-length version of CSP produced in *E. coli*. FMP013 contains the entire C-term and N-term regions of CSP including 19 NANP and 3 NVDP repeats. A cGMP lot of FMP013 was produced and it met of the purity and stability criteria required to advance to CHMI studies (Schwenk et al. (2014) PLoS One 9:e111020). FMP013 was tested with several available vaccine adjuvants however thus far the best immune responses were achieved when FMP013 was combined with ALFQ (Army Liposome Formulation containing QS21). In addition to QS21, ALFQ contains a synthetic version of monophosphoryl lipid A called 3D-PHAD® (Avanti Polar Lipids). In mice, FMP013+ALFQ induced high antibody titers, improved boosting after each of the three vaccinations, high IgG2c and high level protection against transgenic *P. berghei* parasite that contains a functional *P. falciparum* gene. Additionally, FMP013+ALFQ augmented the numbers of splenic germinal center-derived activated B-cells, antibody secreting cells, antigen-specific IFN-γ ELISPOT activity and CD4+ T-cell activity.

Down-selection of vaccines and adjuvants has long relied on preclinical studies in the mouse model. However, promising preclinical leads in mice have not always translated to the development of successful human vaccines. In contrast, several examples of direct translation of vaccine data from Rhesus to humans exist. For example, the selection of AS01 adjuvant over AS02 was performed in Rhesus (Espinosa et al. (2015) J. Infect. Dis. 212:1111-1119; Schwenk et al. (2014) PLoS One 9: e111020; Genito et al. (2017) Vaccine 35:3865-3874); adenovirus primed protein boost showed improved IFN-γ+ T cell responses in both Rhesus (Seth et al. (2017) Vaccine 35:5448-5454) and humans (Porter et al. (2013) Clin. Vaccine Immunol., 20:803-810); the PfSPZ vaccine induced sterilizing immunity in Rhesus against *P. knowlesi* challenge (Khan et al. (BBII) and in humans against *P. falciparum* challenge (Rutgers et al. (1988) Nat. Biotech. 6:1065-1070; Ballou et al. (1987) Lancet 1:1277-1281; Low et al. (2014) Vaccine 32:5041-5048). Likewise, the safety and toxicology data on the AS0 series of adjuvants was collected in Rhesus monkeys.

Pharmaceutical compositions have been developed to act as a malaria vaccine and the pharmaceutical compositions include a novel combination of antigen and an adjuvant. The antigen is a recombinant, nearly full-length circumsporozoite protein (CSP) from *Plasmodium falciparum* that can be expressed in *E. coli*. The composition provides a much more robust immunogenic response than would be expected and is

SUMMARY OF THE INVENTION

The invention relates to pharmaceutical and immunogenic compositions comprising at least one antigen and an adjuvant composition, where the adjuvant composition comprises a saponin and a liposome. The liposome of the composition comprises monophosphoryl lipid A (MPLA), cholesterol and a phospholipid that is in a liquid crystalline state at greater than or equal to 23° C., and the concentration of cholesterol to lipid in the liposome is greater than 50% (mol/mol). The antigen in the composition is a soluble *Plasmodium falciparum* recombinant circumsporozoite protein (rCSP) comprising the amino acid sequence of SEQ ID NO:1, or a *P. falciparum* rCSP peptide that is at least 95% identical to the amino acid sequence of SEQ ID NO:1.

In some embodiments the at least one saponin is QS7, QS18 or QS21 or mixtures thereof. In some embodiments, the concentration of cholesterol to lipid in the liposome is at least about 50.1%, 50.2%, 50.3%, 50.4%, 50.5%, 50.6%, 50.7%, 50.8%, 50.9%, 51%, 52%, 53%, 54%, 55%, 56%, 57%, 58%, 59%, 60%, 61%, 62%, 63%, 64%, 65%, 66%, 67%, 68%, 69%, 70% or 71%. In some embodiments, the phospholipid in the liposome is a phosphatidylcholine (PC) selected from the group consisting of dimyristoyl phosphatidylcholine (DMPC), dipalmitoyl phosphatidylcholine (DPPC) and distearyl phosphatidylcholine (DSPC). In some embodiments, the liposome of the adjuvant composition further comprises a phosphatidylglycerol (PG) selected from dimyristoyl phosphatidylglycerol (DMPG), dipalmitoyl phosphatidylglycerol (DPPG) and distearyl phosphatidylglycerol (DSPG).

In some embodiments, the ratio of the PC to the PG (mol/mol) in the liposome is about 0.5:1, 1:1, 2:1, 3:1, 4:1, 5:1, 6:1, 7:1, 8:1, 9:1, 10:1, 11:1, 12:1, 13:1, 14:1, 15:1. In some embodiments, the amount of MPLA is about 5 mg or less, about 4 mg or less, about 3 mg or less, about 2 mg or less, about 1 mg or less, about 0.9 mg or less, about 0.8 mg or less, about 0.7 mg or less, about 0.6 mg or less, about 0.5 mg or less, about 0.4 mg or less, about 0.3 mg or less, about 0.2 mg or less, about 0.1 mg or less, about 0.09 mg or less, about 0.08 mg or less, about 0.07 mg or less, about 0.06 mg or less, about 0.05 mg or less, about 0.04 mg or less, about 0.03 mg or less, about 0.02 mg or less or about 0.01 mg or less (total weight per ml liposome suspension). In some embodiments, the liposome has a MPLA:phospholipid mole ratio of about 1:5.6 to about 1:880, or about 1:88 to about 1:220.

In some embodiments, the amount of saponin in the liposome is about 1 mg or less, about 0.9 mg or less, about 0.8 mg or less, about 0.7 mg or less, about 0.6 mg or less, about 0.5 mg or less, about 0.4 mg or less, about 0.3 mg or less, about 0.2 mg or less, about 0.1 mg or less, about 0.09 mg or less, about 0.08 mg or less, about 0.07 mg or less, about 0.06 mg or less, about 0.05 mg or less, about 0.04 mg or less, about 0.03 mg or less, about 0.02 mg or less, about 0.01 mg or less (total weight per ml liposome suspension). In some embodiments, the liposome comprises multi-lamellar vesicles (MLV) of about 1 to about 4 μm in diameter or small uni-lamellar vesicles (SUV) of about 50 to about 100 nm in diameter. In some embodiments, the pharmaceutical composition further comprises a physiologically acceptable vehicle.

In some embodiments, the *P. falciparum* rCSP lacks $Met_1$ to $Cys_{25}$ of the N-terminal region of native *P. falciparum* circumsporozoite protein. In some embodiments, the *P. falciparum* rCSP has 18 or 19 NANP (SEQ ID NO:13) repeats. In some embodiments, the *P. falciparum* rCSP has 0 to 3 NVDP (SEQ ID NO:14) repeats. In some embodiments, the *P. falciparum* rCSP has a C-terminal region that lacks ten to fourteen C-terminus amino acid residues of native *P. falciparum* circumsporozoite protein. In some embodiments, the C-terminal residue of the *P. falciparum* rCSP is serine. In some embodiments, the *P. falciparum* rCSP comprises the amino acid sequence of SEQ ID NO:8. In some embodiments, the amount of the *P. falciparum* rCSP antigen is between about 0.01 μg and about 100 μg per dose or per administration. In some embodiments, the amount of *P. falciparum* rCSP antigen is between about 1 μg to about 30 μg per dose per dose or administration. In some embodiments, the adjuvant composition is in an amount from about 0.1 ml to about 10 ml.

The invention also encompasses a method of immunizing a subject against malaria, the method comprising administering a pharmaceutical composition to a subject at least once, wherein the pharmaceutical composition comprises at least one antigen and an adjuvant composition, wherein the adjuvant composition comprises a saponin and a liposome comprising monophosphoryl lipid A (MPLA), cholesterol and a phospholipid that is in a liquid crystalline state at greater than or equal to 23° C., wherein the concentration of cholesterol to lipid in the liposome is greater than 50% (mol/mol), and wherein the antigen is soluble *Plasmodium falciparum* recombinant circumsporozoite protein (rCSP) comprising the amino acid sequence of SEQ ID NO:1, or a *P. falciparum* rCSP peptide that is at least 95% identical to the amino acid sequence of SEQ ID NO:1.

In some embodiments, the pharmaceutical composition is administered to the subject more than once. In some embodiments, the pharmaceutical composition is administered at least three times to the subject, with between 2-6 weeks in between each administration. In some embodiments, the adjuvant composition is in an amount from about 0.1 ml to about 10 ml. In some embodiments, the amount of *P. falciparum* rCSP antigen is between about 1 μg to about 30 μg per dose per dose or administration.

The invention also relates to a pharmaceutical composition comprising a soluble *Plasmodium falciparum* recombinant circumsporozoite protein (rCSP) and an adjuvant composition; wherein the adjuvant composition comprises a saponin and a liposome comprising a monophosphoryl lipid A (MPLA), a phosphatidylcholine (PC), a phosphatidylglycerol (PG), and cholesterol; and the concentration of cholesterol to lipid in the liposome is greater than 50% (mol/mol).

In some embodiments, the soluble *Plasmodium falciparum* recombinant circumsporozoite protein (rCSP) comprises the amino acid sequences of SEQ ID NO:8, SEQ ID NO:9, SEQ ID NO:10, SEQ ID NO:11, or SEQ ID NO:12, or a *P. falciparum* rCSP peptide that is at least 95% identical to the amino acid sequence of SEQ ID NO:8, SEQ ID NO:9, SEQ ID NO:10, SEQ ID NO:11, or SEQ ID NO:12. In some embodiments, the soluble *Plasmodium falciparum* recombinant circumsporozoite protein (rCSP) comprises the amino acid sequence of SEQ ID NO:8 or a *P. falciparum* rCSP peptide that is at least 95% identical to the amino acid sequence of SEQ ID NO:8.

In some embodiments, the saponin is QS7, QS18 or QS21 or mixtures thereof. In some embodiments, the saponin is QS21. In some embodiments, the monophosphoryl lipid A (MPLA) is a synthetic derivative of MPLA. In some embodiments, the monophosphoryl lipid A (MPLA) is 3-deacyl monophosphoryl lipid A. In some embodiments, the phosphatidylcholine (PC) is selected from the group consisting of dimyristoyl phosphatidylcholine (DMPC), dipalmitoyl phosphatidylcholine (DPPC) and distearyl phosphatidylcholine (DSPC). In some embodiments, the phosphatidylcholine is dimyristoyl phosphatidylcholine (DMPC). In some embodiments, the phosphatidylglycerol (PG) is selected from the group consisting of dimyristoyl phosphatidylglycerol (DMPG), dipalmitoyl phosphatidylglycerol (DPPG) and distearyl phosphatidylglycerol (DSPG). In some embodiments, the phosphatidylglycerol (PG) is dimyristoyl phosphatidylglycerol (DMPG).

In some embodiments, the pharmaceutical composition comprises about 1.0 µg, 1.5 µg, 2.0 µg, 2.5 µg, 3.0 µg, 4.0 µg or 5.0 µg rCSP per 50 µl of volume. In some embodiments, the pharmaceutical composition comprises about 1.0 µg, 1.5 µg, 2.0 µg, 2.5 µg, 3.0 µg, 4.0 µg or 5.0 µg rCSP per 1.35 g of liposomes. In some embodiments, the ratio of the PC to the PG (mol/mol) in the liposome is about 0.5:1, 1:1, 2:1, 3:1, 4:1, 5:1, 6:1, 7:1, 8:1, 9:1, 10:1, 11:1, 12:1, 13:1, 14:1, 15:1. In some embodiments, the ratio of the PC to the PG (mol/mol) in the liposome is about 9:1.

In some embodiments, the pharmaceutical composition has a bimodal particle size distribution as determined by dynamic light scattering with local maxima ranging from 70 to 200 nm and from 300 to 800 nm.

DETAILED DESCRIPTION OF THE INVENTION

Figure 1:
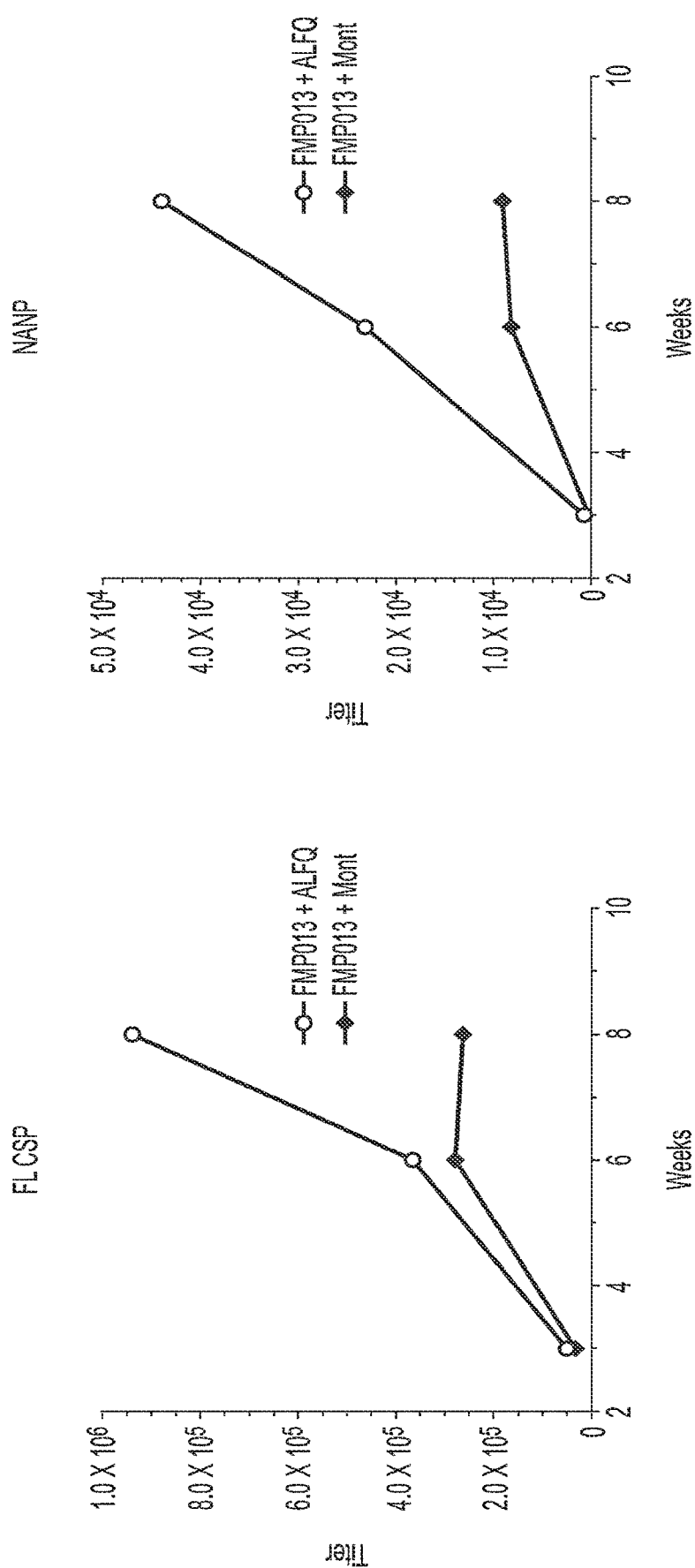
FIG. 1 depicts FMP013+ALFQ vs. FMP013+Montanide immunization titers in mice. (A) Geometric mean (n=8) full-length (FL) CSP titer during 8-week vaccination period. (B) Geomean NANP titer during 8-week vaccination period.

The invention relates to pharmaceutical compositions comprising at least one antigen and an adjuvant composition, where the adjuvant composition comprises a saponin and a liposome. The liposome of the composition comprises monophosphoryl lipid A (MPLA), cholesterol and a phospholipid that is in a liquid crystalline state at greater than or equal to 23° C., and the concentration of cholesterol to lipid in the liposome is greater than 50% (mol/mol). The antigen in the composition is a soluble *Plasmodium falciparum* recombinant circumsporozoite protein (rCSP) comprising the amino acid sequence of SEQ ID NO:1, or a *P. falciparum* rCSP peptide that is at least 95% identical to the amino acid sequence of SEQ ID NO:1.

In some embodiments of the present invention, the adjuvant compositions and methods comprise at least one saponin selected from the group consisting of QS1, QS2, QS3, QS4, QS5, QS6, QS7, QS8, QS9, QS10, QS11, QS12, QS13, QS14, QS15, QS16, QS17, QS18, QS19, QS20, QS21 and QS22, or mixtures thereof. In specific embodiments, the compositions and methods comprise at least one of QS7, QS18 or QS21 or a mixture thereof. In other embodiments, the compositions and methods comprise at least two of QS7, QS18 or QS21 or a mixture thereof. In other embodiments, the compositions and methods comprise QS7, QS18 and QS21 or a mixture thereof.

The concentration of phospholipid in the liposomes of the compositions of the present invention can be from about 0.01 mM to about 1000 mM. In specific embodiments, the concentration of phospholipid in the liposomes of the compositions of the present invention can be from about 1 mM to about 100 mM.

The total amount of saponin in the adjuvant compositions and methods can be about 1 mg, about 0.9 mg, about 0.8 mg, about 0.7 mg, about 0.6 mg, about 0.5 mg, about 0.4 mg, about 0.3 mg, about 0.2 mg, about 0.1 mg, about 0.09 mg, about 0.08 mg, about 0.07 mg, about 0.06 mg, about 0.05 mg, about 0.04 mg, about 0.03 mg, about 0.02 mg, about 0.01 mg, or less (total weight per ml liposome suspension). In other embodiments, total amount of saponin in the compositions and methods can be between about 1 mg and about 0.9 mg, between about 0.9 mg and about 0.8 mg, between about 0.8 mg and about 0.7 mg, between about 0.7 mg and about 0.6 mg, between about 0.6 mg and about 0.5 mg, between about 0.5 mg and about 0.4 mg, between about 0.4 mg and about 0.3 mg, between about 0.3 mg and about 0.2 mg, between about 0.2 mg and about 0.1 mg, between about 0.1 mg and about 0.09 mg, between about 0.09 mg and about 0.08 mg, between about 0.08 mg and about 0.07 mg, between about 0.07 mg and about 0.06 mg, between about 0.06 mg and about 0.05 mg, between about 0.05 mg and about 0.04 mg, between about 0.04 mg and about 0.03 mg, between about 0.03 mg and about 0.02 mg, between about 0.02 mg and about 0.01 mg, or between about 0.01 mg and between about 0.001 mg (total weight per ml liposome suspension).

The compositions and methods of the present invention should have a concentration of cholesterol, relative to the total lipid content of over 50%, such as but not limited to concentrations equal to or greater than about 50.1%, 50.2%, 50.3%, 50.4%, 50.5%, 50.6%, 50.7%, 50.8%, 50.9%, 51%, 52%, 53%, 54%, 55%, 56%, 57%, 58%, 59%, 60%, 61%, 62%, 63%, 64%, 65%, 66%, 67%, 68%, 69%, 70% or 71%. In other embodiments of the present invention, the concentration of cholesterol, relative to the total lipid content, is between about 50.1% and 50.2%, 50.2% and 50.3%, 50.3% and 50.4%, 50.4% and 50.5%, 50.5% and 50.6%, 50.6% and 50.7%, 50.7% and 50.8%, 50.8% and 50.9%, 50.9% and 51%, 51% and 52%, 52% and 53%, 53% and 54%, 54% and 55%, 55% and 56%, 56% and 57%, 57% and 58%, 58% and 59%, 59% and 60%, 60% and 61%, 61% and 62%, 62% and 63%, 63% and 64%, 64% and 65%, 65% and 66%, 66% and 67%, 67% and 68%, 68% and 69%, 69% and 70%, or 70% and 71%.

The compositions and methods of the present invention comprise liposomes containing a neutral phospholipid that is crystalline at greater than or equal to 23° C. In one embodiment, the phospholipid is crystalline at greater than or equal to 23° C. without cholesterol being present. In another embodiment, the phospholipid that is crystalline at greater than or equal to 23° C. is a phosphatidylcholine. Phosphatidylcholines (PCs) are well known lipids containing fatty acids. Examples of PCs that are crystalline at room temperature, without cholesterol being present, include but are not limited to dimyristoyl phosphatidylcholine (DMPC), dipalmitoyl phosphatidylcholine (DPPC) or distearyl phosphatidylcholine (DSPC).

In additional embodiments, the compositions and methods of the present invention comprise at least one type of phosphatidylglycerol (PG) in which the gel to liquid crystalline transition temperature is greater than or equal to 23° C. In a specific embodiment, the PG can be selected from dimyristoyl phosphatidylglycerol (DMPG), dipalmitoyl phosphatidylglycerol (DPPG) or distearyl phosphatidylglycerol (DSPG). When at least one PG is used in the compositions and methods of the present invention, the ratio of total PCs to total PGs (mol/mol) can be about 0.5:1, 1:1, 2:1, 3:1, 4:1, 5:1, 6:1, 7:1, 8:1, 9:1, 10:1, 11:1, 12:1, 13:1, 14:1, 15:1

The compositions and methods of the present invention comprise MPLA. In some embodiments, the amount of MPLA (total weight) is about 5 mg or less, about 4 mg or less, about 3 mg or less, about 2 mg or less, about 1 mg or less, about 0.9 mg or less, about 0.8 mg or less, about 0.7 mg or less, about 0.6 mg or less, about 0.5 mg or less, about 0.4 mg or less, about 0.3 mg or less, about 0.2 mg or less, about 0.1 mg or less, about 0.09 mg or less, about 0.08 mg or less, about 0.07 mg or less, about 0.06 mg or less, about 0.05 mg or less, about 0.04 mg or less, about 0.03 mg or less, about 0.02 mg or less, about 0.01 mg or less (total weight per ml liposome). In other embodiments, the total amount of MPLA in the compositions and methods can be between about 5 mg and about 4 mg, between about 4 mg and about 3 mg, between about 3 mg and about 2 mg, between about 2 mg and about 1 mg, between about 1 mg and about 0.9 mg, between about 0.9 mg and about 0.8 mg, between about 0.8 mg and about 0.7 mg, between about 0.7 mg and about 0.6 mg, between about 0.6 mg and about 0.5 mg, between about 0.5 mg and about 0.4 mg, between about 0.4 mg and about 0.3 mg, between about 0.3 mg and about 0.2 mg, between about 0.2 mg and about 0.1 mg, between about 0.1 mg and about 0.09 mg, between about 0.09 mg and about 0.08 mg, between about 0.08 mg and about 0.07 mg, between about 0.07 mg and about 0.06 mg, between about 0.06 mg and about 0.05 mg, between about 0.05 mg and about 0.04 mg, between about 0.04 mg and about 0.03 mg, between about 0.03 mg and about 0.02 mg, between about 0.02 mg and about 0.01 mg, or between about 0.01 mg and between about 0.001 mg (total weight per ml liposome).

The pharmaceutical compositions and methods of the present composition comprise and antigen, which is a soluble *Plasmodium falciparum* recombinant circumsporozoite protein (rCSP). In one embodiment, the *P. falciparum* rCSP comprises or consists of the amino acid sequence of SEQ ID NO:1. In another embodiment, the *P. falciparum* rCSP comprises an amino acid sequence that is at least 80%, 85%, 86%, 87%, 88%, 89%, 90%, 91%, 92%, 93%, 94%, 95%, 96%, 97%, 98% or 99% identical to the amino acid sequence of SEQ ID NO:1. In one embodiment, the antigen used in the compositions and methods of the present invention are disclosed in WO 2012154199, the entirety of which is incorporated by reference.

In other embodiments, the antigen is the *P. falciparum* rCSP that lacks $Met_1$ to $Cys_{25}$ of the N-terminal region of native *P. falciparum* circumsporozoite protein. In yet another embodiment, the antigen is the *P.falciparum* rCSP that has 18 or 19 NANP (SEQ ID NO:13) repeats. In another embodiment, the antigen is the *P.falciparum* rCSP that has 0 to 3 NVDP (SEQ ID NO:14) repeats. In still another embodiment, the antigen is the *P.falciparum* rCSP that has a C-terminal region that lacks ten to fourteen C-terminus amino acid residues of native *P. falciparum* circumsporozoite protein. In still another embodiment, the antigen is the *P.falciparum* rCSP with a C-terminal residue of serine.

The peptide antigen used in the compositions and methods of the present invention may be fused to another peptide. For example, a region may be added to the antigen peptide to facilitate purification. For example, "histidine tags" ("his tags") or "lysine tags" (the second fusion peptide) may be appended to the first fusion peptide. Examples of histidine tags include, but are not limited to hexaH, heptaH and hexaHN. Additional examples of purification tags are disclosed in Waugh, D. S., Trends in Biotechnology, 23(6): 316-320 (June 2005), and Gaberc-Porekar V. and Menart, V., J. Biochem. Biophys. Methods. 49:335-360 (2001), which are incorporated by reference. Examples of lysine tags include, but are not limited to pentaL, heptaL and FLAG. Additional examples of solubility tags are also disclosed in Waugh, D. S., Trends in Biotechnology, 23(6) 316-320 (June 2005). Such regions may be removed prior to final preparation of the protein. Other examples of a second fusion peptide include, but are not limited to, glutathione S-transferase (GST) and alkaline phosphatase (AP).

The addition of peptide moieties to proteins, whether to engender secretion or excretion, to improve stability and to facilitate purification or translocation, among others, is a familiar and routine technique in the art and may include modifying amino acids at the terminus to accommodate the tags. For example in SEQ ID NO:1, the N-terminus amino acid may be modified to, for example, arginine and/or serine to accommodate a tag. Of course, the amino acid residues of the C-terminus may also be modified to accommodate tags. One particularly useful fusion protein comprises a heterologous region from immunoglobulin that can be used solubilize proteins.

The fusion proteins of the current invention can be recovered and purified from recombinant cell cultures by well-known methods including, but not limited to, ammonium sulfate or ethanol precipitation, acid extraction, anion or cation exchange chromatography, phosphocellulose chromatography, hydrophobic interaction chromatography, affinity chromatography, e.g., immobilized metal affinity chromatography (IMAC), hydroxylapatite chromatography and lectin chromatography. High performance liquid chromatography ("HPLC") may also be employed for purification. Well-known techniques for refolding protein may be employed to regenerate active conformation when the fusion protein is denatured during isolation and/or purification.

For example, the antigen used in the compositions and methods of the present invention is the *P.falciparum* rCSP comprising or consisting of the amino acid sequence of SEQ ID NO:8. In another embodiment, the *P. falciparum* rCSP comprises an amino acid sequence that is at least 80%, 85%, 86%, 87%, 88%, 89%, 90%, 91%, 92%, 93%, 94%, 95%, 96%, 97%, 98% or 99% identical to the amino acid sequence of SEQ ID NO:8. The term "FMP013" as used herein refers to a peptide that consists of the amino acid sequence of SEQ ID NO:8.

For example, the antigen used in the compositions and methods of the present invention is the *P.falciparum* rCSP comprising or consisting of the amino acid sequence of SEQ ID NO:9. In another embodiment, the *P. falciparum* rCSP comprises an amino acid sequence that is at least 80%, 85%, 86%, 87%, 88%, 89%, 90%, 91%, 92%, 93%, 94%, 95%, 96%, 97%, 98% or 99% identical to the amino acid sequence of SEQ ID NO:9.

For example, the antigen used in the compositions and methods of the present invention is the *P.falciparum* rCSP comprising or consisting of the amino acid sequence of SEQ ID NO:10. In another embodiment, the *P. falciparum* rCSP comprises an amino acid sequence that is at least 80%, 85%, 86%, 87%, 88%, 89%, 90%, 91%, 92%, 93%, 94%, 95%, 96%, 97%, 98% or 99% identical to the amino acid sequence of SEQ ID NO:10.

For example, the antigen used in the compositions and methods of the present invention is the *P.falciparum* rCSP comprising or consisting of the amino acid sequence of SEQ ID NO:11. In another embodiment, the *P. falciparum* rCSP comprises an amino acid sequence that is at least 80%, 85%, 86%, 87%, 88%, 89%, 90%, 91%, 92%, 93%, 94%, 95%, 96%, 97%, 98% or 99% identical to the amino acid sequence of SEQ ID NO:11.

For example, the antigen used in the compositions and methods of the present invention is the *P.falciparum* rCSP comprising or consisting of the amino acid sequence of SEQ ID NO:12. In another embodiment, the *P. falciparum* rCSP comprises an amino acid sequence that is at least 80%, 85%, 86%, 87%, 88%, 89%, 90%, 91%, 92%, 93%, 94%, 95%, 96%, 97%, 98% or 99% identical to the amino acid sequence of SEQ ID NO:12.

"Identity" per se has an art-recognized meaning and can be calculated using published techniques. By a polypeptide being at least, for example, 95% "identical" to a reference amino acid sequence, it is intended that the amino acid sequence of the polypeptide is identical to the reference sequence, except that the amino acid sequence may include up to five mutations per each 100 amino acids of the reference amino acid sequence. For example, to obtain a peptide having an amino acid sequence at least 95% identical to a reference amino acid sequence, up to 5% of the amino acids in the reference sequence may be deleted or substituted with another residue, or a number of residues up to 5% of the total residues in the reference sequence may be inserted into the reference sequence.

As a practical matter, whether any peptide is at least 60%, 65%, 70%, 75%, 80%, 85%, 90%, 92%, 94%, 95%, 96%, 97%, 98% or 99% identical to an amino acid sequence of the presence invention can be determined using known computer programs. One method for determining the best overall match between a query sequence and a subject sequence, also referred to as a global sequence alignment, can be determined using the FASTDB computer program based on the algorithm of Brutlag et al. (Comp. App. Biosci. 6:237 245 (1990)). In a conventional nucleotide sequence alignment, the query and subject sequences are both DNA sequences; however, an RNA sequence can be compared by converting U's to T's. The results of the global sequence alignment are reported in terms of percent identity. In one embodiment of the present invention, the parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

The present invention also provides methods of generating an immune response in a subject comprising administering the pharmaceutical compositions as described herein. In one embodiment, the pharmaceutical compositions can be administered to a subject at least once. In another embodiment, the pharmaceutical compositions can be administered to the subject more than once. In another embodiment, the pharmaceutical compositions can be administered at least three times to the subject.

If the compositions of the present invention are administered more than once, there can be anywhere from 0 days (all doses on same day) to about 56 days (about 8 weeks) in between doses. In one embodiment, there are between about 2-6 weeks in between each administration of the pharmaceutical compositions of the present invention.

The compositions and methods comprise the antigens as disclosed herein. The compositions and methods comprise the antigen in an amount of from about 0.01 µg to about 100 µg per dose or per administration. In more specific embodiments, the amount of antigen used in the methods or compositions is from about 0.1 μg to about 50 μg per dose or administration. In more specific embodiments, the amount of antigen used in the methods or compositions is from about 0.5 μg to about 40 μg per dose or administration. In more specific embodiments, the amount of antigen used in the methods or compositions is from about 1 μg to about 30 μg per dose or administration. In more specific embodiments, the amount of antigen used in the methods or compositions is from about 1.25 μg to about 20 μg per dose or administration. In more specific embodiments, the amount of antigen used in the methods or compositions is from about 1.5 μg to about 15 μg per dose or administration. In more specific embodiments, the amount of antigen used in the methods or compositions is from about 1.75 μg to about 10 μg per dose or administration. In more specific embodiments, the amount of antigen used in the methods or compositions is from about 2.0 μg to about 7.5 μg per dose or administration. In more specific embodiments, the amount of antigen used in the methods or compositions is from about 2.25 μg to about 5.0 μg per dose or administration. In more specific embodiments, the amount of antigen used in the methods or compositions is about 2.5 μg per dose or administration.

The compositions and methods disclosed herein also comprise the adjuvant compositions as discussed herein. The compositions and methods of the present invention comprise the adjuvant composition in an amount from about 0.1 ml to about 10 ml. in more specific embodiments, the amount of adjuvant composition is from about 0.2 ml to about 8 ml, or from about 0.5 ml to about 5 ml, or from about 1 ml to about 2.5 ml.

EXAMPLES

Methods
Preparation of Liposomes

Dimyristoyl phosphatidylcholine (DMPC), dimyristoyl phosphatidylglycerol (DMPG), cholesterol and synthetic monophosphoryl lipid A (MPLA) derivative 3-deacyl monophosphoryl lipid A (3D-PHAD®) were obtained from Avanti Polar Lipids (Alabaster, Ala.). ALF contained DMPC:DMPG phospholipids (9:1 M ratio), cholesterol (43 mol %) and 3D-PHAD® (0.26 mM). For ALFQ liposomes, the cholesterol concentration was adjusted to 55 mol %. Briefly, multilamellar liposomes were formed using the lipid deposition method by combining DMPC and cholesterol (both in chloroform), DMPG and 3D-PHAD® (in chloroform:methanol; 9:1 v/v). Multilamellar liposomes were then microfluidized (LV1 instrument, Microfluidics, Westwood, Mass.) to yield small unilamellar liposomes, which were sterile filtered and stored in lyophilized form at 4° C. Final cholesterol concentration was quantified by colorimetric assay.

Preparation of Vaccine Formulations

FMP013 was cGMP-grade nearly full-length recombinant 3D7 strain P. falciparum CSP expressed and purified from E. coli. A total of 2.5 mg of FMP013 was present in each vaccine dose. Liposomal formulation compositions are summarized in Table 1. For ALF formulation, lyophilized FMP013 was reconstituted and added to dried liposomes. For ALFQ formulation, reconstituted FMP013 was mixed with Alhydrogel (Brenntag Biosector, Frederikssund, Denmark) before adding to dried liposomes. For ALFQ, QS-21 (Desert King International, San Diego, Calif.) was mixed with small unilamellar liposomes before adding FMP013. Montanide formulations containing 70% Montanide ISA 720 VG (SEPPIC Inc., Fairfield, N.J.) and 30% antigen (v/v) were vigorously vortexed for 25 min and emulsification was confirmed by a water surface dispersion test.

Protein and Liposome Analysis

Particle size dispersion was measured on a Zetasizer Nano S (Malvern, Worcestershire, United Kingdom). Thermal stability was assessed by incubating the formulations at +37° C. (kinetic stability) or room temperature and analyzing the samples at different time-points by SDS-PAGE followed by silver staining (Pierce Silver Stain Kit, Thermo Fisher Scientific, Waltham, Mass.). Western blot was performed to stain CSP specific degradation products using polyclonal mouse anti-CSP (1:2500) essentially as described previously.

Immunization of Mice and Challenge

Female C57BL/6J mice (The Jackson Laboratory, Bar Harbor, Me., USA) were immunized intramuscularly (IM) with 50 ml of the vaccines by injection in alternate rear thighs at 0, 3, and 6 weeks. The animals were bled three weeks after the first and second immunizations and two weeks after the third immunization. Protective efficacy of vaccines was assessed using transgenic P. berghei (Tr-Pb) sporozoites expressing a functional full-length P. falciparum CSP gene [2]. Animals were challenged 15 days after the last immunization with 100 ml intravenous (IV) injection of 3000 Tr-Pb sporozoites into the caudal vein, as described by Porter et al. Blood-stage parasitemia was detected by microscopy of giemsa-stained thin blood smear. Animals were considered protected if parasitemia was not detected during a two-week observation period following challenge. Ten naïve mice were included in each study to verify a 100% infection rate of the transgenic parasite.

Germinal Center B-Cell and Antibody Secreting Cell (ASC) Analysis

Cell suspension from spleens were prepared as described. For phenotypic analysis, pooled cells were stained with mAb specific for CD19 (1D3), CD95 (Jo2), and GL7 (GL7) (BD Biosciences), counted by FACS (BD Biosciences) and data was analyzed using FlowJo 10 software (Tree Star). For detecting CSP-specific IgG antibody secreting cells (ASC) an ELI-SPOT was conducted. Splenocytes in complete RPMI containing 10% fetal bovine albumin and $10^{-6}$% v/v 2-mercaptoethanol, 1 mM glutamine, 1 mM pyruvate, and Gibco™ MEM non-essential amino acids were plated on 10 mg/ml FL CSP coated 96-well Multi-Screen HTS IP plates (EMD Millipore) and incubated for 4 h at +37° C. ASC were detected by sequential incubation with biotinylated rabbit anti-mouse IgG (0.5 g/mL; Southern Biotech) overnight at +4° C., NeutrAvidin horseradish peroxidase (1:1000; Thermo Scientific) for 1 h at room temperature, and filtered 3,30-diaminobenzidine substrate (Sigma-Aldrich, St. Louis, Mo.) in 0.03% v/v hydrogen peroxide. Spots were counted using an AID ELISPOT Reader and software (Autoimmun Diagnostika). For a subsequent experiment, the frequency of CSP-specific B cells was determined by ELISPOT analysis following the instructions of the manufacturer (U-CyTech), i.e., splenocytes were polyclonally activated with R848 and IL-2 for two days, cell number determined, and then plated on CSP-coated ELISPOT plates for 6 h at 37° C.

T-Cell Analysis by Flow Cytometry

Cell suspensions of mouse splenocytes were prepared essentially as described. Stimulator cells were prepared by pulsing EL4 (Clone TIB-39, ATCC, Manassas, Va.) suspension cells with peptide pools of 15mers overlapping by 11 amino acids covering the PfCSP protein sequence. The peptides pools were "N-term pool" (aa 1-107; 24 peptides total), "repeat pool" (aa 97-283; 12 peptides total, only unique 15mers in this repeat sequence included), and "C-term pool" (aa 273-397; 29 peptides total). A "Mega pool" was made from all 65 peptides. T-cell analysis was performed on freshly isolated splenocytes from individual mice (n=5) stimulated with peptide pulsed EL4 cells. Briefly, $1\times10^6$ splenocytes from individual mice and $1.5\times10^5$ pulsed EL4 stimulator cells were incubated for 6 h at 37° C. in 5% CO2. BD Golgi Plug™ (BD Biosciences) was added 1 h into the incubation to block cytokine release and stored at 4° C. overnight. The samples were stained for viability using the LIVE/DEAD® Fixable Blue Dead Cell Stain Kit for UV excitation from Molecular Probes® (Life Technologies) and blocked for non-specific staining using Mouse BD Fc Block™ (BD Biosciences). The samples were surface-stained with the following antibodies (fluorochrome): CD4-RM4-5 (BD Horizon V500), CD3e-500A2 (Alexa 700) (BD Biosciences), KLRG1-2F1 (PerCP-eFluor710) (eBioscience), CD8a-53-6.7 (BV785), CD127-A7R34 (BV421) and CD27-LG.3A10 (APC) (Biolegend). Following separate fixation and permeablization steps, the samples were stained intracellularly with the following fluorochrome-labeled antibodies: CD44-IM7 (Cy7PE), CD8a-53-6.7(BV785), TNF-a-MP6-XT22 (BV605) (Biolegend), CD3e-500A2 (Alexa 700), IFN-c-XMG1.2 (Alexa 488) and IL-2-JES6-5H4 (PE) (BD Biosciences). The data were acquired using a LSR II (BD Biosciences) and analyzed using FlowJo 10 software (Tree Star). The gating scheme for T-cell analysis has been detailed. A small positive threshold was established to account for negative data in a non-biased manner after background subtraction from non-pulsed EL4 samples. The criterion for inclusion in the dataset was a frequency greater than the mean+2SD frequency of the ALFQ adjuvant control group.

IFN-cELISPOT

IFN-cELISPOT responses were assessed with fresh splenocytes in group pools (5 mice/group) in quadruplicate wells. Splenocyte group pools were plated at 400,000 cells/well with 135,000 peptide-pulsed EL4 stimulator cells/well on multiscreen MAHAS4510 plates (EMD Millipore) coated with 1 mg/well of a rat anti-mouse IFN-γ antibody (Clone R4-6A2, BD Biosciences). PMA/lonomycin-stimulated splenocytes served as assay controls. The plates were incubated at 37° C. in 5% $CO_2$ for 40 h and biotinylated rat anti-mouse IFN-c antibody (clone XMG1.2, BD Biosciences) was added at 1 mg/ml for 3 h at room temperature, followed with 1:800 dilution of peroxidase-labeled streptavidin (KPL). Spots were developed and counted as above.

Cytokine profiling by pro-inflammatory panel kit Freshly prepared splenocytes were stimulated with CSP-peptide pools described above at 1.25 mg/mL final concentration for 48 h. Meso Scale Discovery's 10-plex mouse pro-inflammatory panel kit (1L1β, KC, IL-2, IL-4, IL-6, IL-10, IL-12p70, IL-13, IFN-γ, TNF-α) was used to analyze culture supernatants according to the manufacturer's protocol. Plates were read using a MESO Quick-Plex SQ120 (Meso Scale Diagnostics).

Statistics

FL, NANP and subclass ELISA data were log transformed. For data sets with multiple groups, data was analyzed by ANOVA and p-values were corrected by Tukey's multiple comparisons test using GraphPad Prism software. Comparisons between two groups were made using two-tailed T-test. Statistically significant difference in group means was indicated in figures as *, $P<0.05$; , $P<0.01$; *, $P<0.001$; ****, $P<0.0001$. After parasite challenge, Dunnett's method was used to establish significant delay in patency over naïve control mice and Fisher's exact test was used to determine significant differences in protection between vaccinated groups.

Rhesus Monkeys

Colony bred adult rhesus macaques of Indian origin (*Macaca* mulatta), were housed at the WRAIR animal facility and used under an IACUC-approved protocol number 13-MVD-12L. Monkeys used were naïve and had never been used in an experimental study. The animal environment was controlled with a 12:12-hour light:dark cycle. All animals were quarantined for a period of 4 weeks and free from any overt clinical signs of illness, deemed to be in good health and tested negative for Macacine herpesvirus 1, measles, Simian Retrovirus, Simian Immunodeficiency Virus and Simian T-cell Leukemia Virus, and tuberculin skin test. Animals were pair housed, fed a commercial diet (Lab Diet 5038, Purina Mills International) and provided water ad libitum. Environmental enrichment was provided in accordance with WRAIR Veterinary Service Programs standing operating procedures.

Rhesus Vaccination and Bleeds

The schedule for vaccination was 0, 1 and 2 months. Lyophilized CSP was resuspended with 0.4 mL sterile water and brought up to a volume of either 0.8 ml or 1.6 ml with PBS. From the CSP suspension, 0.6 mL was combined with 0.6 ml of ALFQ and rolled for 1 hr±20 min. Rhesus monkeys (n=6) were anesthetized and the thigh area was shaved. Three doses of either 0.5 or 1 ml of the vaccine was administered i.m. in the outer thigh muscle one month apart. Group 1: 3×20 µg FMP013+0.5 ml ALFQ; Group 2: 3×20 µg FMP013+1 ml ALFQ and Group 3: 3×40 µg FMP013+1 ml ALFQ. Rhesus monkeys were bled 2 weeks prior to the first dose, on days 1, 3, and 7 after vaccine administration to monitor toxicological effects on blood chemistry/cell counts and then at 2 weeks after each vaccination for serology.

Rhesus Safety and Tolerability Assessment

Before any immunization or manipulation, macaques were sedated with Ketamine HCl at 5-10 mg/kg in combination with acepromazine at 0.05-0.1 mg/kg. Rectal temperature was taken at days 0, 1, 3, and 7 after each immunization. Injection sites were examined at baseline and then 1, 3, and 7 days after vaccine administration. Sites were examined for signs of reaction, including skin warmth, erythema, swelling, muscle induration, ulceration, abscess, or other abnormalities. The grading scales for skin warmth, muscle swelling, erythema and muscle induration was as follows: 0, absent; 1, mild; 2, moderate; 3, severe. Hematologic parameters, including complete blood count and complete serum chemistry analyses, were performed on days 1, 3, and 7 after each immunization. Two ml of blood was collected from femoral vein in Vacutainer-Becton Dickinson tubes for whole blood blood and serum analysis for cell counts WBC, RBC, HGB, HCT, MCV, MCH, MCHC, PLT, RDW-CV, MPV, % NEUT, % LYMPH, % MONO, % EOS, % BASO, #NEUT, #LYMPH, #MONO, #EOS, #BASO) and chemistry (Glucose, BUN, Creatinine, Sodium, Potassium, Chloride, Carbon Dioxide, Calcium, Phosphorus, Cholesterol, Triglycerides, Total Protein, Albumin, AST, ALT, LDH, CK, ALKP, GGT, Total Bilirubin). Fever cutoff was any temperature more than 2 standard deviations above the 6-month overall average for each animal.

Inhibition of Liver Stage Development Assay (ILSDA)

The NF54 strain of *Plasmodium falciparum* (Pf) sporozoites (obtained from salivary gland dissections) were mixed with a positive control monoclonal anti-CSP monoclonal NFS1 or polyclonal Rhesus IgG at a final concentration of 360 μg/ml or 180 μg/ml and incubated at room temperature for 20 minutes. The sporozoites-antibody mixtures were then introduced into the wells containing cryopreserved human hepatocytes (BioReclamation IVT) and incubated at 37° C. for 3 hours to allow sporozoites to infect hepatocytes. After the 3-hour incubation period, hepatocytes were washed with fresh culture media to remove non-invaded sporozoites and incubated at 37° C. for 96 hours. The RNA from the cells was then harvested for downstream quantitative real-time PCR (qRT-PCR) analysis. Pf 18s rRNA level were quantified to determine the level of inhibition of liver stage development.

Example 1

Female C57BL/6 mice were immunized intramuscularly with 50 μl of the vaccines by injection in alternate rear thighs at 0, 3, and 6 weeks. The animals were bled three weeks after the first and second immunizations and two weeks after the third dose. Each dose of the vaccine contained 2.5 μg of FMP013 formulated with ALFQ or a commercially available oil-based adjuvant Montanide ISA 720 VG (Montanide) as a control. Montanide was used as a benchmark for immunogenicity as is known to induce very high antibody response in mice when combined with investigational malaria vaccines, and has also been used in human clinical trials. Following each of 3 vaccinations in C57BL/6 mice (n=8), mice were monitored 1-2 times daily and showed no local and systemic adverse reactions and no skin abnormalities, weight loss or lethargy. ELISA conducted against the full-length CSP antigen (FL CSP) and the NANP repeat peptide showed that Montanide group mice sero-converted all mice against FL CSP and 7/8 mice against NANP after the first dose; the second dose boosted antibody titers; no further boosting was observed post-third dose (FIG. 1). ALFQ seroconverted all mice against both FL CSP and NANP after the first dose, induced higher FL CSP titers than Montanide post-second and post-third dose, and showed substantial boosting of antibody titers (FIG. 1).

Example 2

Figure 2:
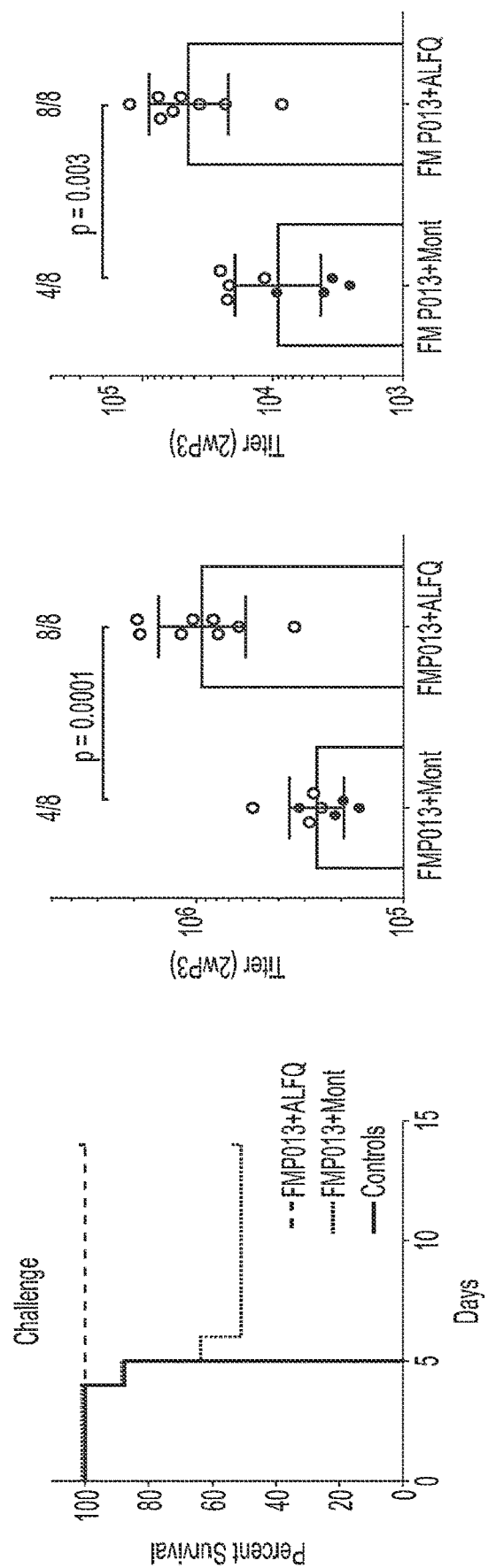
FIG. 2 depicts the protective efficacy and immunogenicity of the compositions of the present invention. Left, Kaplan-Meyer survival following transgenic *Plasmodium berghei* (Tr-Pb) challenge. Mice were considered protected if no blood-stage parasites were observed during the two-week follow-up. Middle, FL titer and protection status of individual mice at 2 weeks post-third dose. Right, NANP titer and protection status of individual mice at 2 weeks post-third dose. Number of protected and total challenged mice are shown on top of each bar. Red symbols: protected; black symbols: non-protected mice. P-values are for individual two-sided T-tests on log transformed titers. Open bars are geo. means, whiskers represent 95% CI.

To evaluate the protective efficacy, the vaccinated mice were challenged 2 weeks after the final (third) dose with intravenous injection of 3000 transgenic strain *P. berghei* (Tr-Pb) sporozoites. Parasitemia was observed in all naïve control mice by day 5 (FIG. 2 left panel). Montanide showed 50% sterile protection (4/8), while ALFQ protected 100% of mice (8/8). The magnitude of NANP titers correlated with protection status of challenged mice, as has been observed in controlled human malaria infection (CHMI). Significant differences between ALFQ and Montanide adjuvanted FMP013 were determined by two-tailed t tests for titers on the day before challenge. The ALFQ group FL titer was 4-fold higher than Montanide (P=0.0001) after the third dose (FIG. 2 middle). The NANP titer profiles for both vaccine formulations (FIG. 2 right) were similar to the FL profiles. ALFQ NANP titers were 5-fold higher than Montanide (P=0.03) post-third dose. Thus, FMP013 was able to induce higher antibody titers and confer more protection when adjuvanted with ALFQ than with Montanide.

Figure 3:
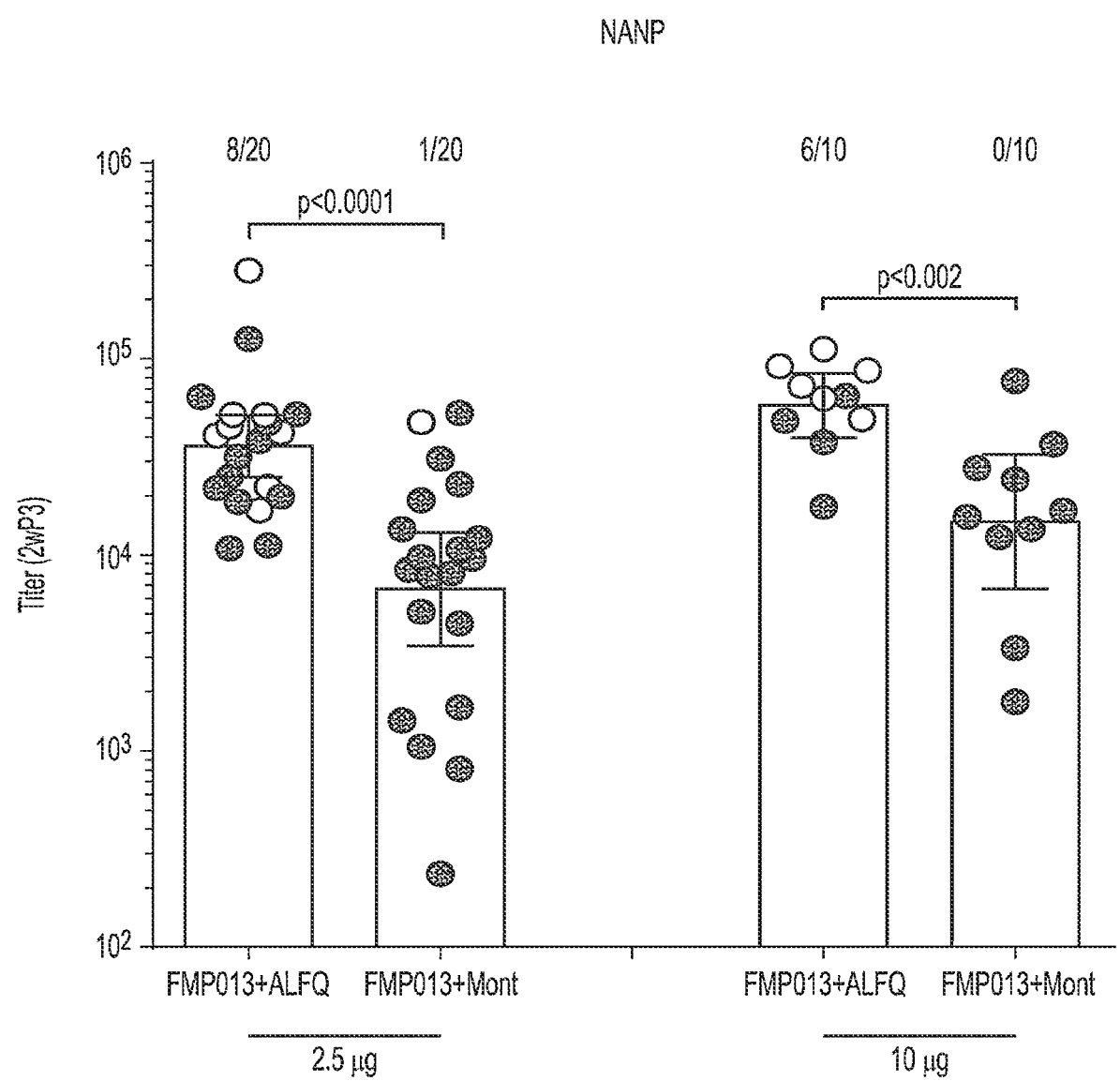
FIG. 3 depicts repeat challenge studies. NANP titer and protection status of individual mice at 2 weeks post-third dose for repeat challenge studies at 2.5 µg FMP013 (n=20) or 10 µg FMP013 (n=10). The number of protected and total challenged mice are shown on top of each bar. Red symbols: protected; black symbols: non-protected mice. P-values are for individual two-sided T-tests on log transformed titers. Open bars are geo. means, whiskers represent 95% CI.
Figure 4:
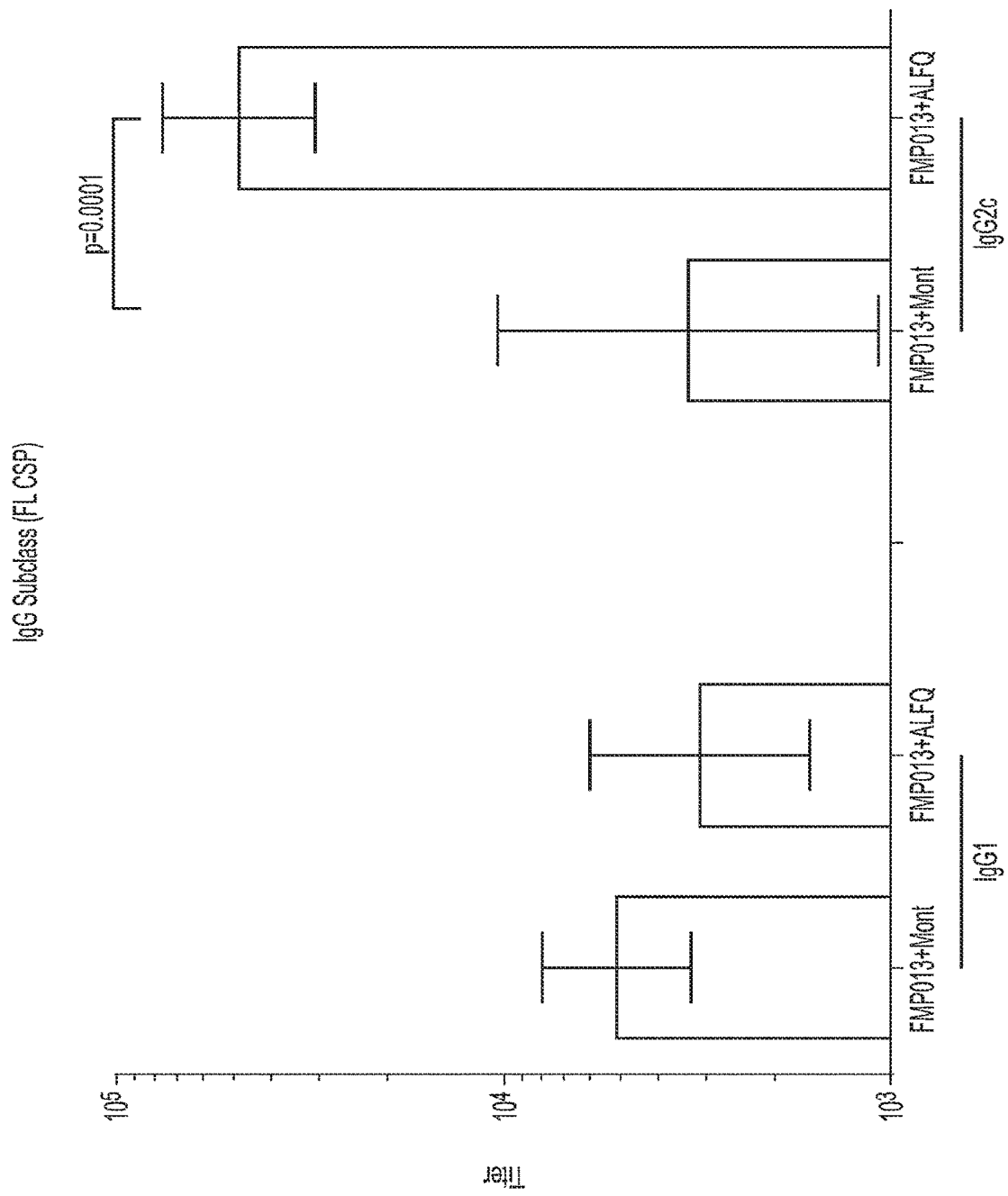
FIG. 4 depicts antibody subclasses in mice. Geometric mean anti-FL CSP IgG1 (left) and IgG2c (right) titers (n=8) from first challenge study at 2 weeks post-third dose. P-value is for individual two-sided T-tests on log transformed titers. Whiskers represent 95% CI.

ALFQ and Montanide adjuvants were further compared in two subsequent challenge studies with a larger mouse sample size, which allowed for more statistical power to discern differences in protection between ALFQ and Montanide adjuvanted FMP013. In both studies, three doses of 2.5 μg FMP013 (n=10) were tested and the combined NANP and protection data was analyzed (FIG. 3, left bars). ALFQ showed higher NANP response (P<0.0001) and higher protection (40% vs. 5%, P=0.02, Fisher's exact test) compared to Montanide (FIG. 3). In one of the studies, ALFQ and Montanide were compared at 10 μg FMP013 dose (n=10). At this elevated dose, higher NANP titers (P=0.002) and protection (60% vs. 0%, P=0.01, Fisher's exact test) were again observed in the ALFQ group compared to Montanide (FIG. 4, right bars). FMP013 with ALFQ reproducibly showed higher titers, better boosting and higher protection than Montanide.

Example 4

Sera from the first challenge experiment collected 2 weeks after the third dose were analyzed for IgG subclasses (FIG. 4). No significant difference in IgG1 levels were observed across adjuvants. In sharp contrast to the IgG1 data, ALFQ adjuvanted IgG2c responses were 14-fold higher than Montanide (P=0.0001). Elevated levels of IgG2c antibodies suggested a $TH_1$ biased immune response was induced by ALFQ, which has shown to correlate with protection in past studies.

Example 5

Figure 5A:
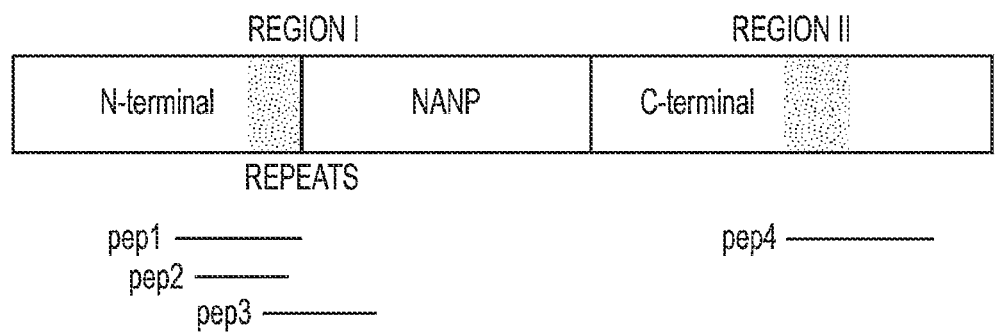
FIG. 5 depicts region-specific immunogenicity in mice. (A) Location of Region I and Region II and location of peptides spanning the CSP primary structure are shown with respect to the N-terminal, C-terminal and the NANP repeats. (B) Group mean (n=8) absorbance at 415 nm against each peptide at a serum dilution factor of 1:1000 for Montanide (filled bars) and ALFQ (open bars) from the first study.
Figure 5B:
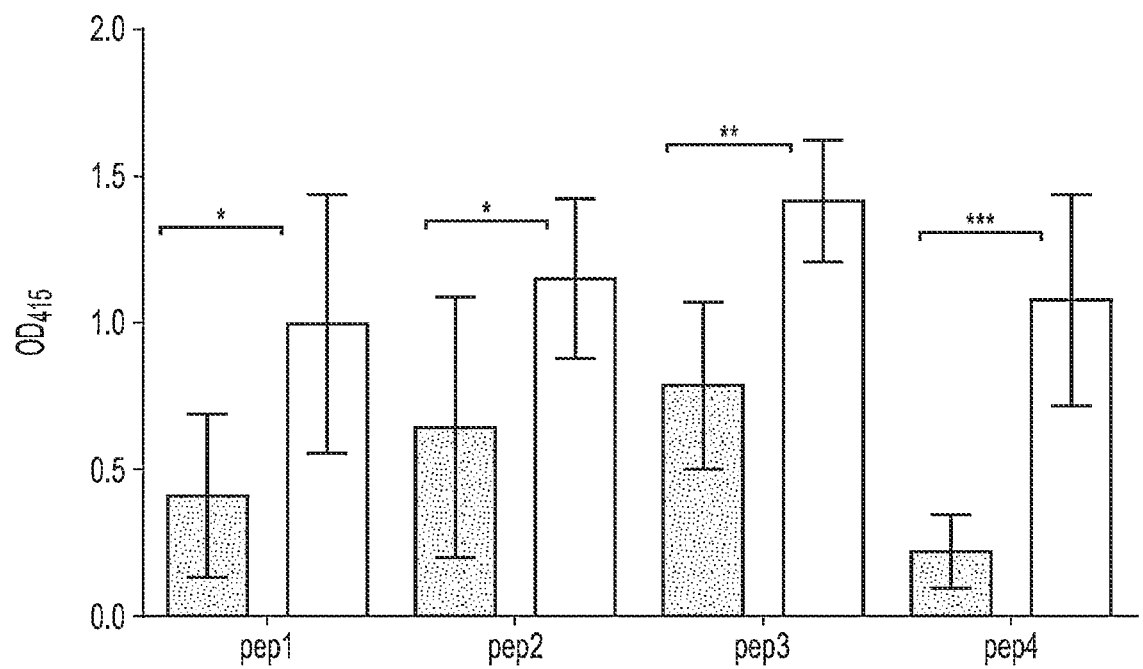

CSP contains conserved motifs called "Region I" in the N-terminal and "Region II" in the C-terminal of the molecule (FIG. 5). Both N-terminal and C-terminal is believed to be of functional significance vis-a-vis hepatocyte binding and invasion. CSP N-terminal region is essential to rescue mammalian liver infectivity in transgenic sporozoites. Further the sporozoite injected by the mosquito has its N-terminal region "shielding" the C-terminal region. At the time of invasion the N-terminal region is proteolytically cleaved and a monoclonal antibody that blocks process can also block invasion. Several T cell epitopes have been mapped to the N-terminal region, further bolstering the rationale of including the N-terminal in a CSP vaccine. CSP vaccine that induces antibodies against the N-terminal has never been developed. To determine if ALFQ formulation enhanced immunogenicity key epitopes, a mapping ELISA was conducted on the ALFQ and control Montanide group mouse sera. ELISA against Region I-spanning peptides (pep1, pep2, and pep3) and a Region II-spanning peptide (pep4) showed higher antibody binding in the ALFQ group as compared to Montanide (FIG. 5). These data, combined with the FL and NANP ELISA data, show an overall increase in titers across the CSP molecule by the FMP013+ALFQ vaccine.

Example 6

Four groups of 6 monkeys each were given either a half dose or a full dose of FMP013+ALFQ vaccine. The groups were divided as follows:
  Group 1: 3×20 μg FMP013+0.5 ml ALFQ at week 0-4-8
  Group 2: 3×20 μg FMP013+1 ml ALFQ at week 0-4-8
  Group 3: 3×40 μg FMP013+1 ml ALFQ at week 0-4-8
  Group 4: 2×40 μg FMP013+1 ml ALFQ at week 0-4; 1x 8 μg FMP013+0.2 ml ALFQ at week 8.

Figure 6:
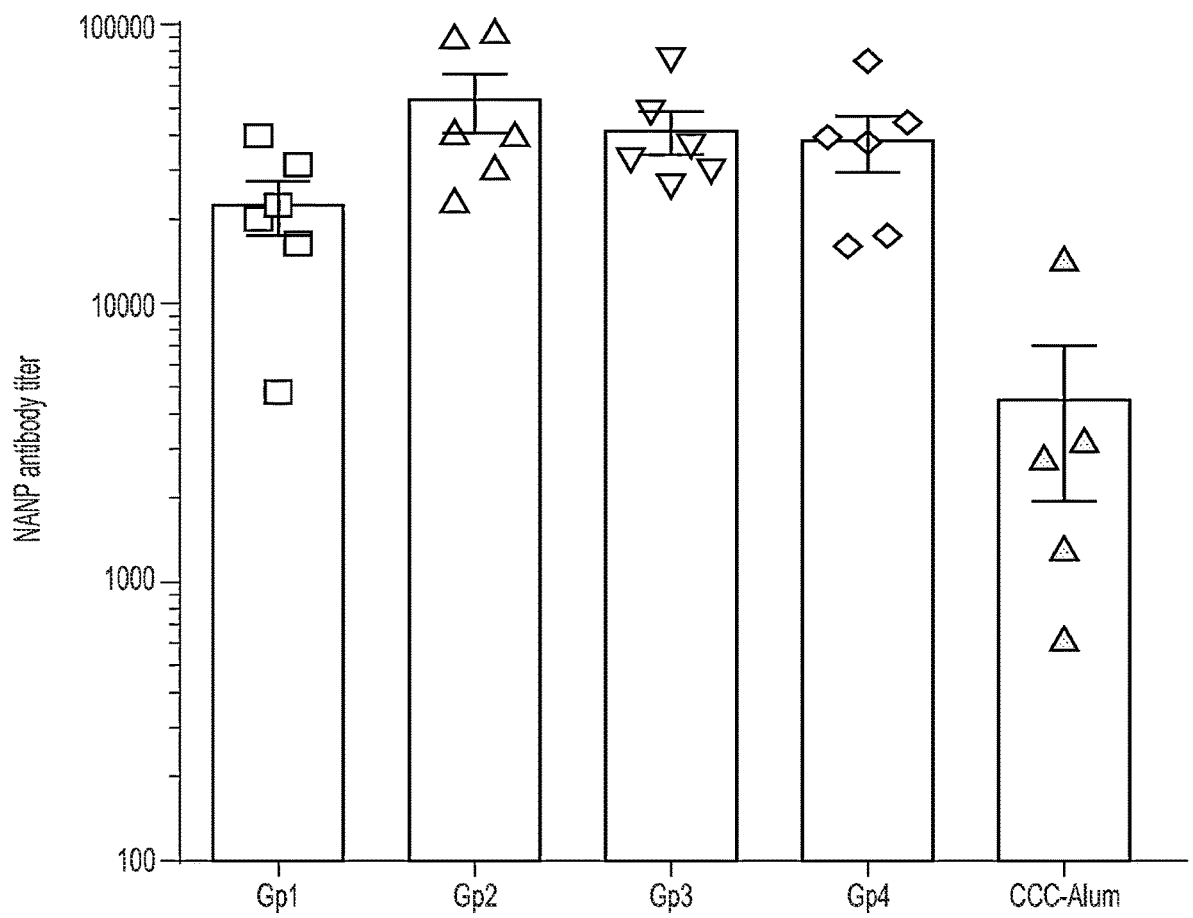
FIG. 6 depicts the immunogenicity of the FMP013 vaccine in Rhesus: NANP ELISA titers after three doses of the vaccines in Groups (Gp) 1 to 4. ELISA titer of Rhesus vaccinated with the FMP013 with Alum adjuvant (CCC-Alum) was used as a comparator vaccine.

Monkeys showed no signs of local and systemic reactivity. ELISA against the NANP repeat region was conducted to determine the immunogenicity of FMP013+ALFQ. As a comparator titers of a group of animals vaccinated with FMP013+Alum (FIG. 6: CCC+Alum) are shown. Potent NANP ELISA titer (>10,000 titers) confirmed that the ALFQ adjuvanted FMP013 vaccines were significantly superior to FMP013+Alum.

Example 7

Figure 7:
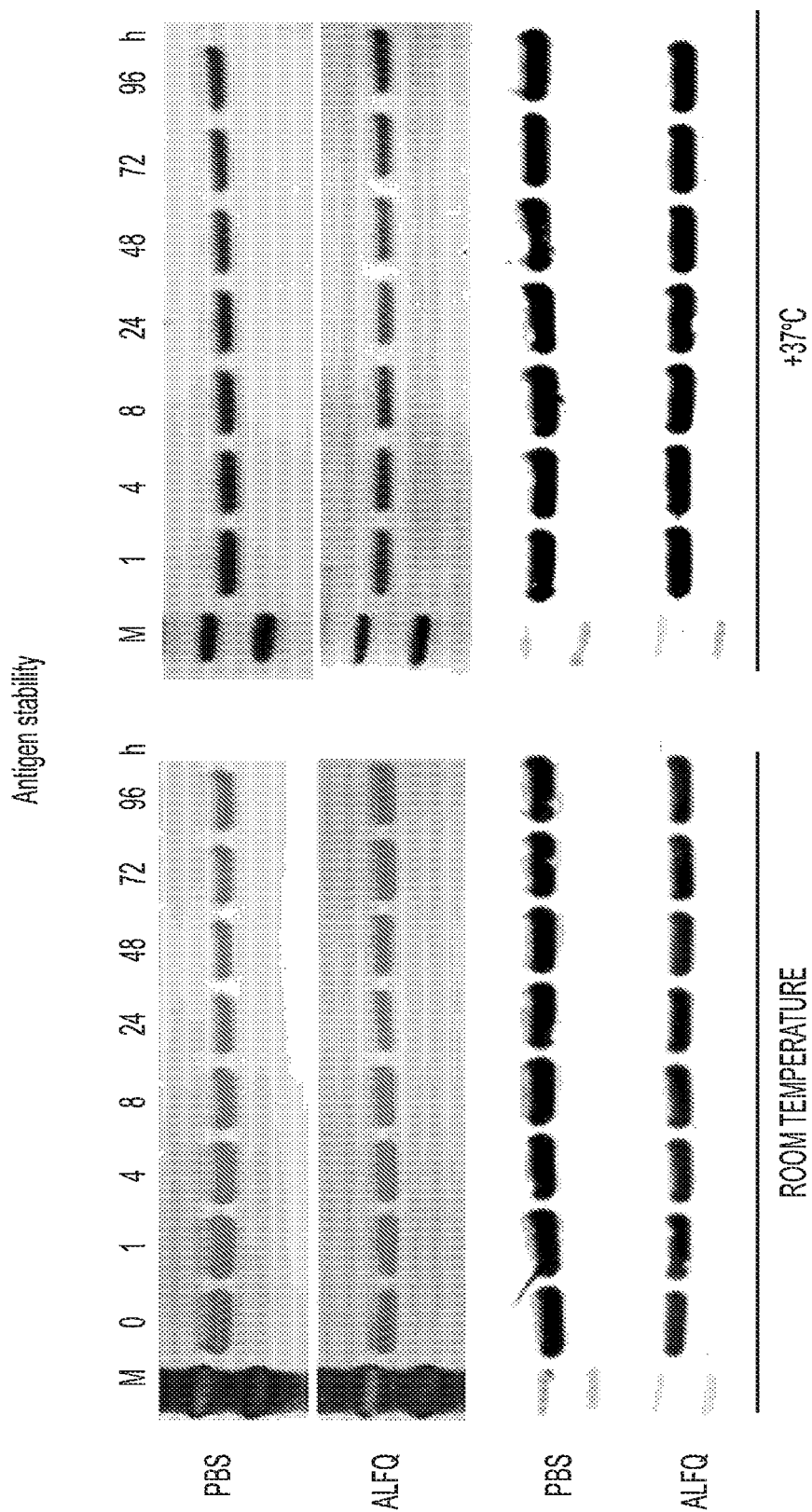
FIG. 7 depicts room temperature and kinetic stability (37° C.) of the rCSP antigen. The top two panels are coomassie stained SDS-PAGE gels and bottom two panels are western blot of the same using CSP antibodies.

The lyophilized FMP013 protein was formulated with PBS control or with ALFQ adjuvant and protein integrity was monitored over time at room temperature and at +37° C. (kinetic stability) using coomassie blue stained gel and by western blot using CSP antibodies (FIG. 7). In the 96 hr room temperature stability assay, the FMP013+PBS and FMP013+ALFQ maintained full stability for up to 4 hours as determined by coomassie blue staining and western blot. In the 96 hour kinetic stability assay, FMP013 was again found to maintain stability for at least 4 hours at 37° C.

Example 8

In order to down-select an adjuvant, FMP013 was formulated in three liposomal preparations and a commercially available oil-based adjuvant Montanide ISA 720 VG (Montanide) was used as a control. The composition of the liposomal formulations, ALF, ALFQ, and ALFQ, are detailed in Table 1. The FMP013 cGMP product was stored as frozen bulk protein (B) and in lyophilized form (L). ALFQ formulations with both bulk (ALFQ-B) and lyophilized FMP013 (ALFQ-L) were evaluated while ALF and ALFQ were tested with only the lyophilized FMP013. Following each of 3 vaccinations in C57BL/6 mice (n=8), mice were monitored 1-2 times daily for local and systemic adverse reactions at the vaccine site, significant weight loss, scruffiness of the coat and lethargy, with none detected during the observation period. ELISA conducted against the full-length CSP antigen (FL) and the NANP repeat peptide showed that Montanide group mice sero-converted after the first dose; the second dose boosted antibody titers; however, no further boosting was observed post-third dose. ALF and ALFQ FL titers did not differ significantly from Montanide throughout the course of the experiment, while ALFQ-B and ALFQ-L induced higher FL titers than Montanide post-second and post-third dose. ALFQ-L group FL titer was 4-fold higher than Montanide (P=0.0001), 3-fold higher than ALFQ (P=0.0007) and 5-fold higher than ALF (P<0.0001) post-third dose. In these studies, the ALFQ-B and ALFQ-L performed similarly in this experiment and a repeat experiment (data not shown). The NANP titer profiles for the five vaccine formulations were similar to the FL profiles. ALFQ-B and ALFQ-L NANP titers were both ~5-fold higher than Montanide (P=0.01 for both comparisons) and no difference between ALF, ALFQ and Montanide NANP titers was observed post-third dose. To evaluate the protective efficacy of the vaccines, mice were challenged 2 weeks after the third dose with sporozoites of transgenic strain *P. berghei* (Tr-Pb). Parasitemia was observed in all naïve control mice by day 5. Montanide showed 50% sterile protection (4/8), while ALFQ-B protected 83% (7/8) and ALFQ-L protected 100% of mice (8/8). ALF and ALFQ protected similarly to Montanide, at 50% and 38% (4/8 and 3/8) respectively.

TABLE 1

Amount (μg) of each component in a 50 μL dose of ALF, ALFA, and ALFQ formulated vaccines administered to mice. The contents listed for ALFQ apply to both ALFQ-B and ALFQ-L.

| Component | ALF | ALFA | ALFQ |
| --- | --- | --- | --- |
| CSP (μg) | 2.5 | 2.5 | 2.5 |
| DMPC (μg) | 70 | 70 | 700 |
| DMPG (μg) | 7.9 | 7.9 | 79 |
| Cholesterol (μg) | 33.4 | 33.4 | 541 |
| MPLA (μg) | 20 | 20 | 20 |
| Aluminum Hydroxide (μg) | — | 30 | — |
| QS21 (μg) | — | — | 10 |

ALFQ and Montanide adjuvants were further compared in two subsequent challenge studies. Whereas the previous experiment compared multiple groups, the direct comparison of only two groups allowed for more statistical power to discern differences in protection between ALFQ and Montanide adjuvanted FMP013. In both studies, three doses of 2.5 μg FMP013 (n=10) were tested and the combined NANP and protection data was analyzed. ALFQ showed higher NANP response (P<0.0001) and higher protection (40% vs. 5%, P=0.02) compared to Montanide. In one of the studies, ALFQ and Montanide were compared at 10 μg FMP013 dose (n=10). At this elevated dose, higher NANP titers (P=0.002) and protection (60% vs. 0%, P=0.01) were again observed in the ALFQ group compared to Montanide. Slide positivity data was also examined for time-to-blood stage patency. Indeed the 2.5 μg and the 10 μg dose groups of CSP+ALFQ group both showed approximately a one day increase in time to patency as compared to the naïve controls (p=0.004 and p=0.005 for 2.5 μg and 10 μg, respectively), while Montanide showed no delay compared to the naïve controls. To rule out any non-specific protective role of the adjuvant, 10 mice per group were vaccinated with 3 doses, 3 weeks apart, with 2.5 CSP+ALFQ and 10 mice received equivalent volumes of ALFQ adjuvant. None of the adjuvant controls were protected while 3 of 10 CSP+ALFQ vaccinated mice were protected in this experiment. Despite the observed variability in sterile protection outcomes between experiments, the CSP+ALFQ vaccinated groups reproducibly showed high titer, excellent boosting and a varying degree of sterile protection against transgenic parasite challenge.

Sera from the first challenge experiment collected 2 weeks after the third dose were analyzed for IgG subclasses. While IgG1 responses of the ALFQ group were higher than ALF (P=0.04), no other significant difference in IgG1 levels were observed across adjuvants. In sharp contrast to the IgG1 data, ALFQ-L IgG2c responses were 8-fold higher than Montanide (P<0.0001), 7 fold higher than ALF (P=0.0008) and 9 fold higher than ALFQ (P=<0.0001). IgG2c responses of the ALFQ-B group were similarly higher than the other groups. The serum antibody avidity against FL and NANP antigens were measured, but no significant differences between adjuvant groups were observed. Elevated levels of IgG2c antibodies suggested a TH1 biased immune response was induced by ALFQ.

CSP contains conserved motifs Region I and Region II that are believed to be of functional significance vis-a-vis hepatocyte binding and invasion. In particular, residues around Region I have been shown to be conserved proteolytic cleavage sites, and are targeted by an invasion inhibitory antibody, 5D5. To determine if ALFQ formulation enhanced immunogenicity to these key epitopes, a mapping ELISA was conducted on the ALFQ-L and control Montanide group sera from the first mouse study. ELISA against Region I-spanning peptides (pep1, pep2, and pep3) and a Region II-spanning peptide (pep4) showed higher antibody binding in the ALFQ group as compared to Montanide. These data, combined with the FL and NANP ELISA data, show an overall increase in titers across the CSP molecule by the ALFQ adjuvant.

To investigate the ability of ALFQ-adjuvanted FMP013 to activate B-cells, groups of 6 mice were administered ALFQ-L- or Montanide-adjuvanted FMP013. Two weeks post-first dose, splenocytes were harvested (n=2) and stained for phenotypic markers of activated germinal center (GC)-derived B cells (GL7 and CD95). Cells were gated for CD19 and the CD19+GL7+CD95+ cells were quantified by flow-cytometry. As compared to the naïve animals, the percentage of CD19+GL7+CD95+ cells were 2-fold higher in the Montanide group and 14-fold higher in the ALFQ group. Furthermore, CSP-specific antibody secreting cells (ASC) were quantified in pooled splenocytes using a B-cell ELISPOT at 3 weeks after the first dose and 3 weeks after a second dose (n=2). The ALFQ group showed a higher number of splenocyte-derived ASC than the Montanide group at both the post-first and post-second dose time points. Together these data show improved antibodies and protection induced by ALFQ associated with improved B-cell activation and ASC formation in the spleen.

Five mice were immunized three times at three week intervals with 2.5 µg of bulk FMP013 in either Montanide or ALFQ. Control mice received ALFQ alone with PBS. Two weeks after the third dose, splenocytes from mice were harvested, stimulated with the antigen, and evaluated for T-cell activity by IFN-γ ELISPOT, flow-cytometric determination of the frequency of IFN-γ, TNF-α and IL2 producing CD4+ and CD8+ T-cells and quantification of secreted cytokines by multiplex cytokine array (Mesoscale). IFN-γ ELISPOT revealed that the number of CSP-specific IFN-γ producing splenocytes was higher in the FMP013+ALFQ vaccinated mice as compared to FMP013+Montanide. ELISPOT activity was mainly focused to the repeat and lesser to the C-term region. Flow-cytometric analysis confirmed that ALFQ group showed a higher frequency of CD4+ T-cells that were positive for IFN-γ as well as TNF-α as compared to mice vaccinated with FMP013+Montanide. This CD4+ T-cell response was also highly focused towards the repeat region of CSP. Remarkably, no cytokine positive CD8+ T-cells were detected (data not shown). In an effort to profile the immune responses induced by the various vaccine formulations, 10 different cytokines were quantified by Mesoscale. The FMP013+ALFQ group splenocytes produced higher levels of IFN-γ, IL-2 and TNF-α as compared to FMP013+Montanide, which only produced low levels of IL-2. In all three assays described above the ALFQ adjuvant control mice showed no CSP-specific T-cell activity. Overall, these data along with the antibody subclass profile established that FMP013+ALFQ induced a $TH_1$ biased response. In these groups of mice, CSP-specific ASC frequency was also determined using a B-cell ELISPOT assay against FL CSP and similar to the data in, the CSP+ALFQ induced a significant 5-fold higher frequency than Montanide (P=0.005) and 9-fold higher than ALFQ control mice (P=0.002).

Figure 8:
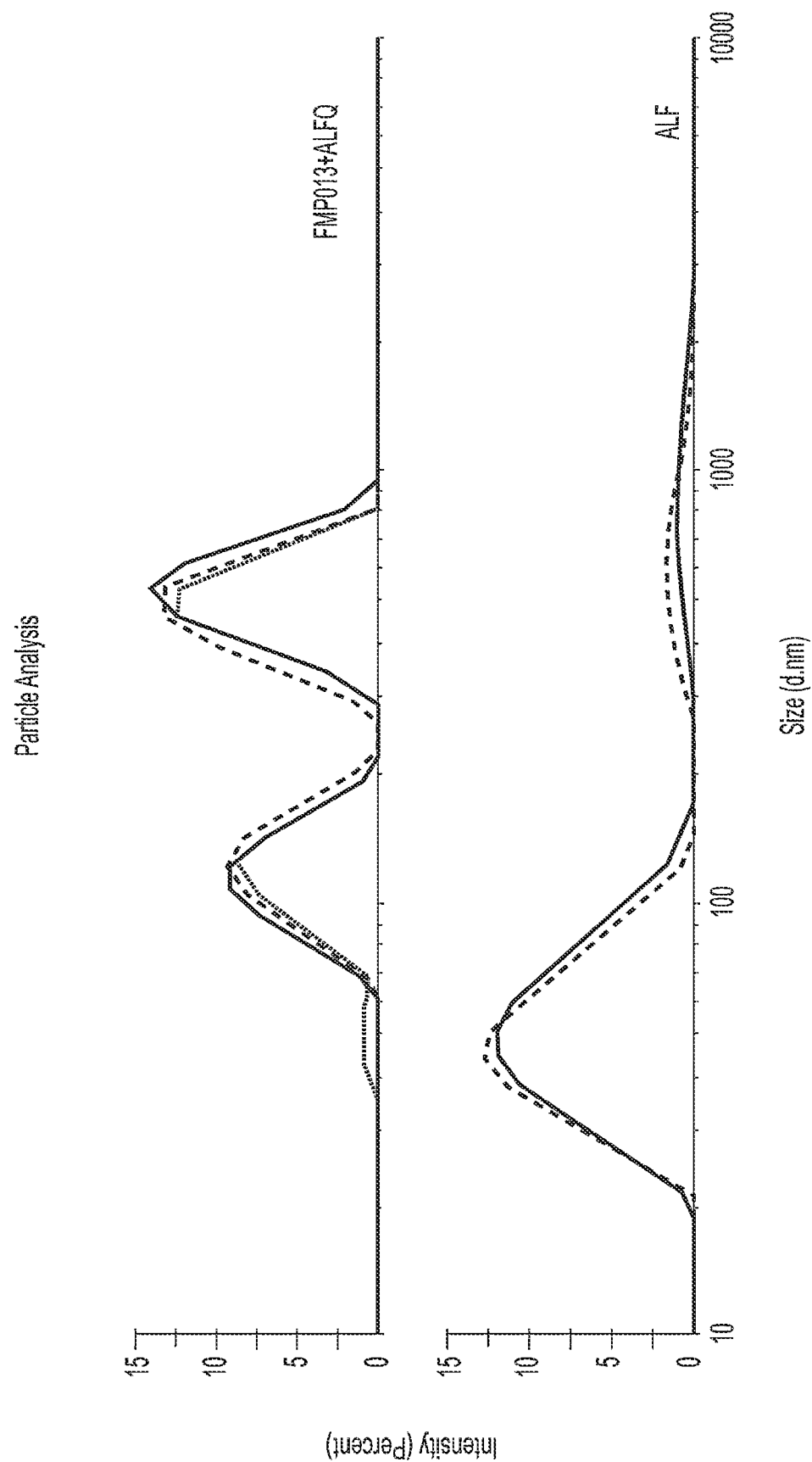
FIG. 8 depicts particle size analysis by dynamic light scattering. Each line (light gray, gray, or black) represents an independent reading.

The stability and integrity of the FMP013 antigen formulated in ALFQ were studied at room temperature and at +37° C. (kinetic stability). At room temperature, no band broadening or degradation was observed in PBS or ALFQ for up to 4 h on a silver stained gel. At the 8 h time-point, some weakening of FMP013 band intensity was noted in PBS, but not in ALFQ. Indeed, FMP013 was stable in ALFQ for up to 96 h, as was confirmed by the corresponding CSP specific western blot. FMP013 was also found to be stable for 96 h at +37° C. in a kinetic stability assay. Analysis by dynamic light scattering (DLS) determined the average particle size of the liposomes in ALF adjuvant to be 55±13 nm. After the addition of QS-21 and FMP013, the liposome size increased and the profile became more poly-dispersed (FIG. 8). This particle profile of ALFQ formulated FMP013 vaccine was stable for at least 8 h at room temperature. These data suggest that formulation in ALFQ does not modify or accelerate degradation of the antigen at ambient and physiological temperatures.

Example 9

Rhesus Toxicology

Figure 9:
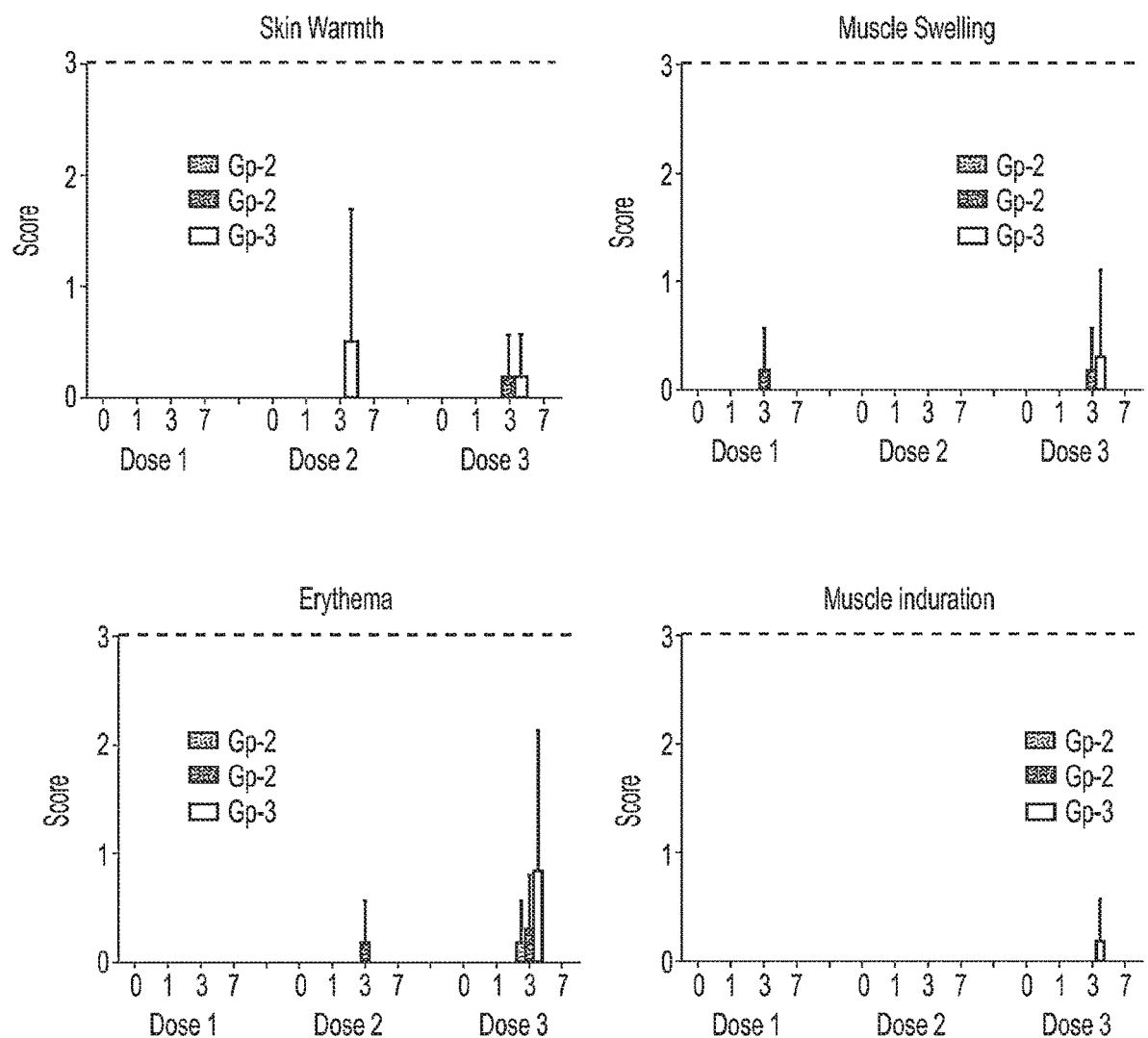
FIG. 9 depicts the mean groups score of local adverse events on day 1, 3, and 7 after dose 1, dose 2 and dose 3 of the vaccine in Rhesus monkeys. Groups 1, 2 and 3 are shown in blue, red and green bars.

Group-1 received 20 µg FMP013 (half dose antigen) in 0.5 ml ALFQ (half dose adjuvant); Group-2 received 20 µg FMP013 in 1 ml ALFQ (full dose adjuvant) and Group-3 received 40 ug FMP013 in 1 ml AFLQ (full dose of both antigen and adjuvant). Three half dose and full dose vaccines administered at 3-wk interval in Rhesus showed no major systemic adverse effects on body weight or food consumption. Local reactions were scored and group mean was plotted in FIG. 9. Compared to the half dose adjuvant (Group 1 blue bar), local vaccine site reactions were more common in full-dose groups-2 and -3 with transient skin warmth and mild erythema at the vaccine site (green and red bars). Likewise, muscle swelling and induration were more common in groups-2 and -3. All of the local vaccine site reactions resolved by day 7. No wounds, ulceration, or abscesses were observed at the vaccine site. In Group-3, two of six monkeys developed a mild ecchymosis reaction around the vaccine site on day 3 post 2nd dose; both ecchymosis reactions cleared completely by day 7.

Figure 10:
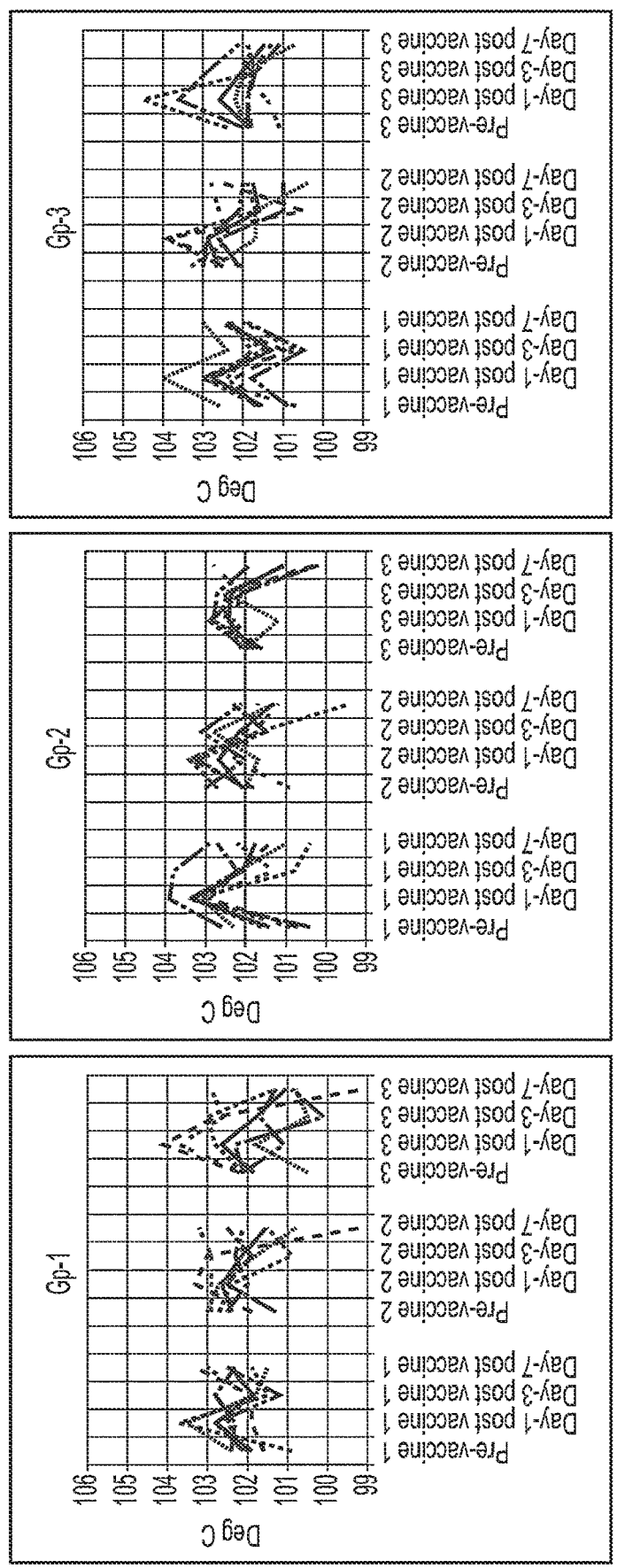
FIG. 10 depicts the temperature of individual Rhesus monkeys (various colors) and the mean temperature of the group (Black) on day 1, 3 and 7 following vaccination.

Transient fevers were noted in Rhesus after vaccination (FIG. 10). On average 0.5 to 1 degree elevation in temperature was seen on day-1 post vaccination which resolved by day 7. Group-1 showed mild fever in 2 of 6 monkeys that lasted for 72 hrs but resolved by day 7. In Group-2, 5/6 animals had mild fever after each of the first two vaccinations and in Group-3, 2/6 monkeys had fever. Animals with the highest temperature spikes on day-1 post vaccination were in Group-3 (FIG. 10). Blood chemistry changes on day 1, 3 and 7 after vaccination showed transient effects of the vaccine on glucose level (increased on day 1), creatinine kinase (increased on day 1), blood urea nitrogen (dipped on day 1) however all these changes were resolved by day 7.

Figure 11:
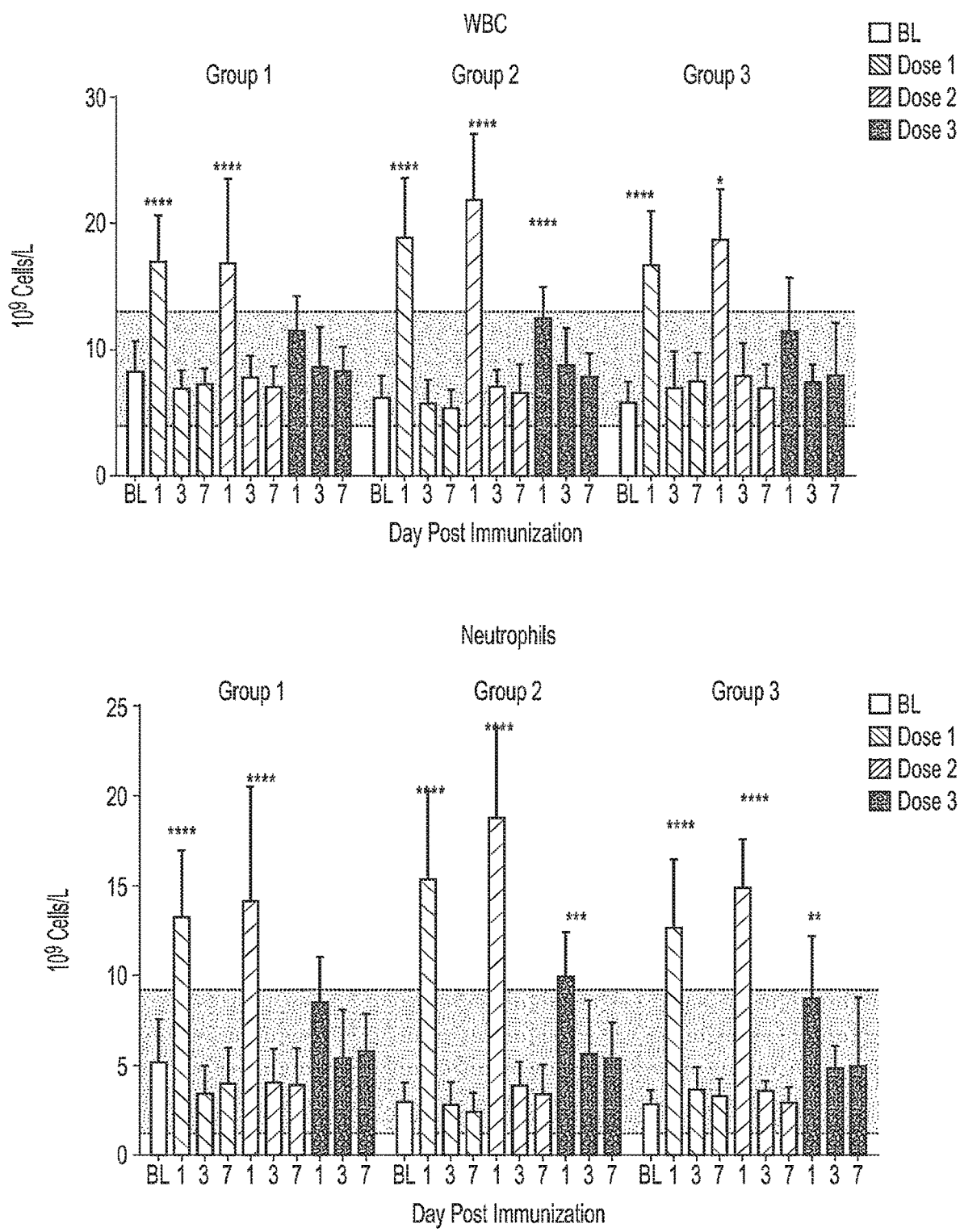
FIG. 11 depicts hematological observations in Rhesus monkeys. Bars are group mean+SD at each time point. BL=baseline level pre-immunization. Shaded region is reference range for normal limits for each parameter. Stars denote statistical significance over baseline (p<0.05, Two-way ANOVA, compare columns within groups, Dunnett's method for multiple comparisons).
Figure 11:
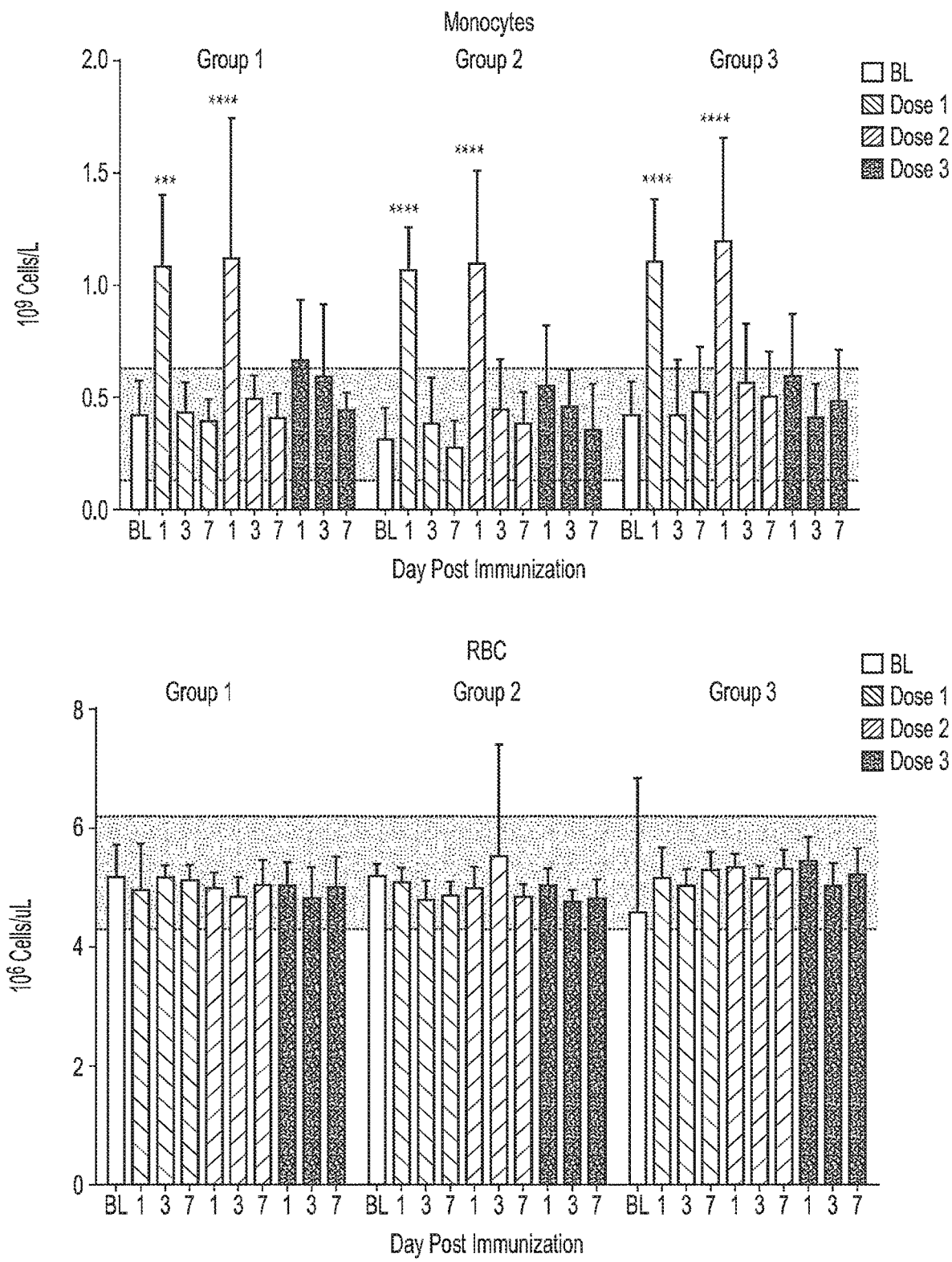
Figure 12A:
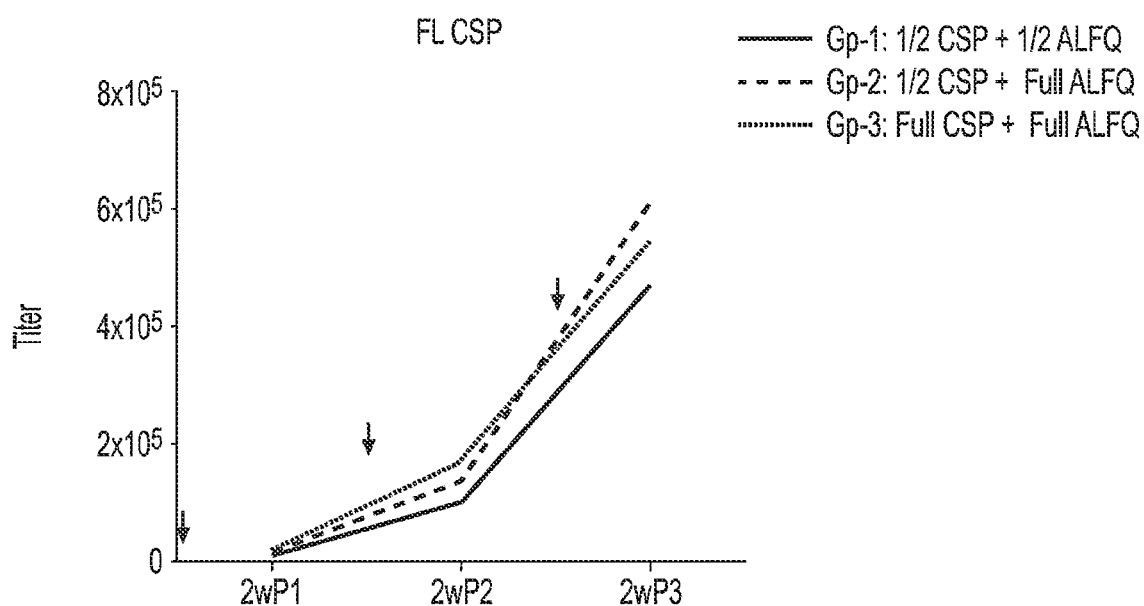
FIG. 12 depicts mean ELISA titers for each group against Full length CSP (A), C-term peptide (C) and NANP peptide (E) at 2 weeks post 1st, 2nd and 3rd vaccination in Rhesus monkeys. Arrows indicate the timing for vaccinations. Bars are mean titer against full-length (B), C-term (D) and NANP repeat (F) at 2 week post 3rd dose (SE of mean and individual data points shown).
Figure 12B:
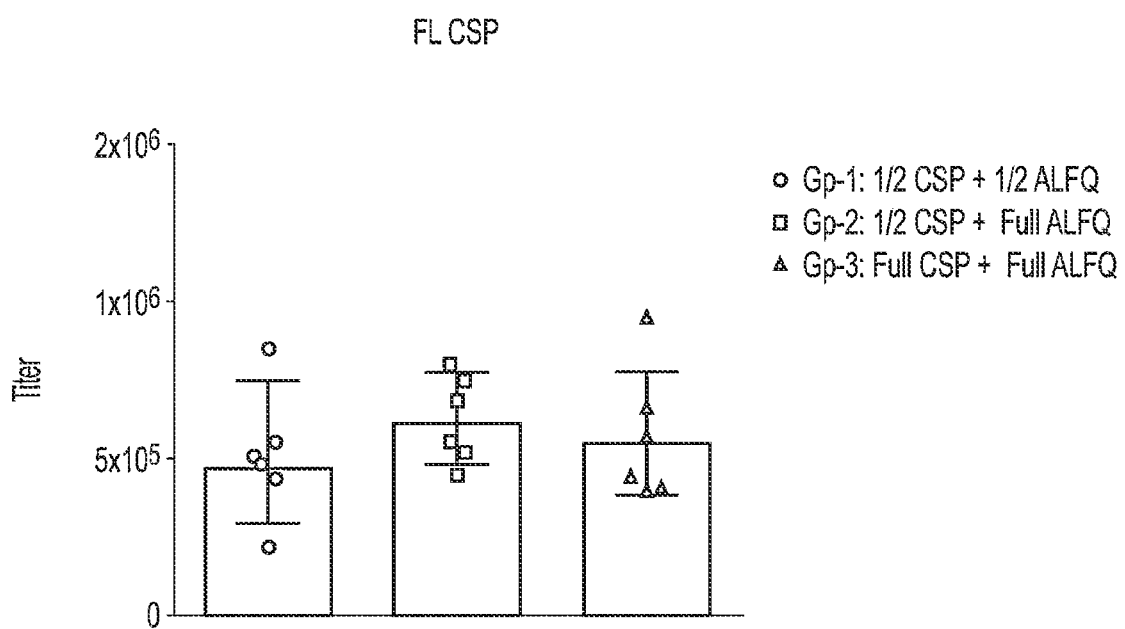
Figure 12C:
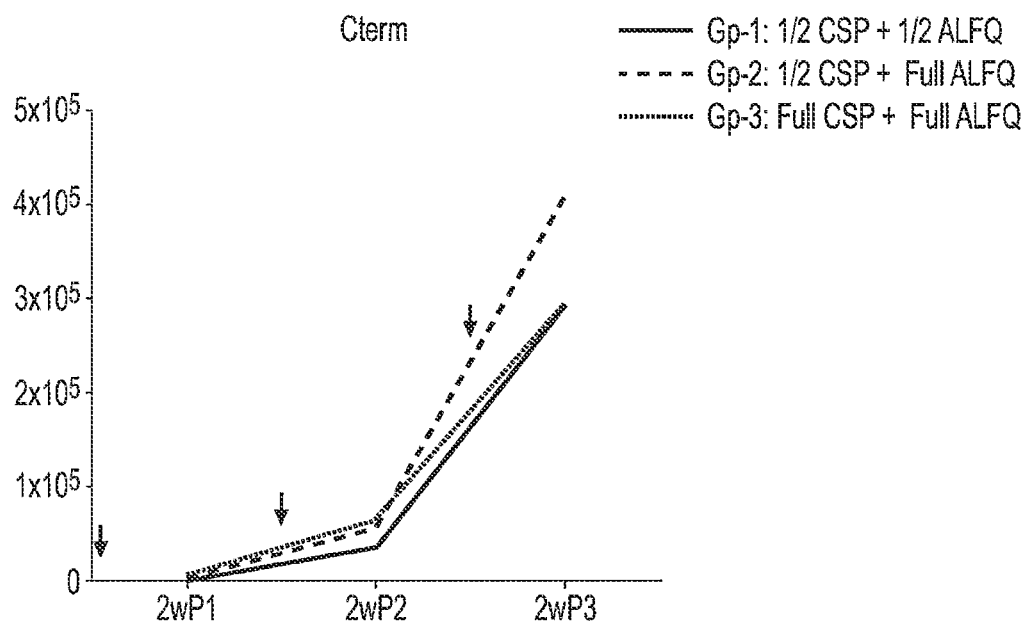
Figure 12D:
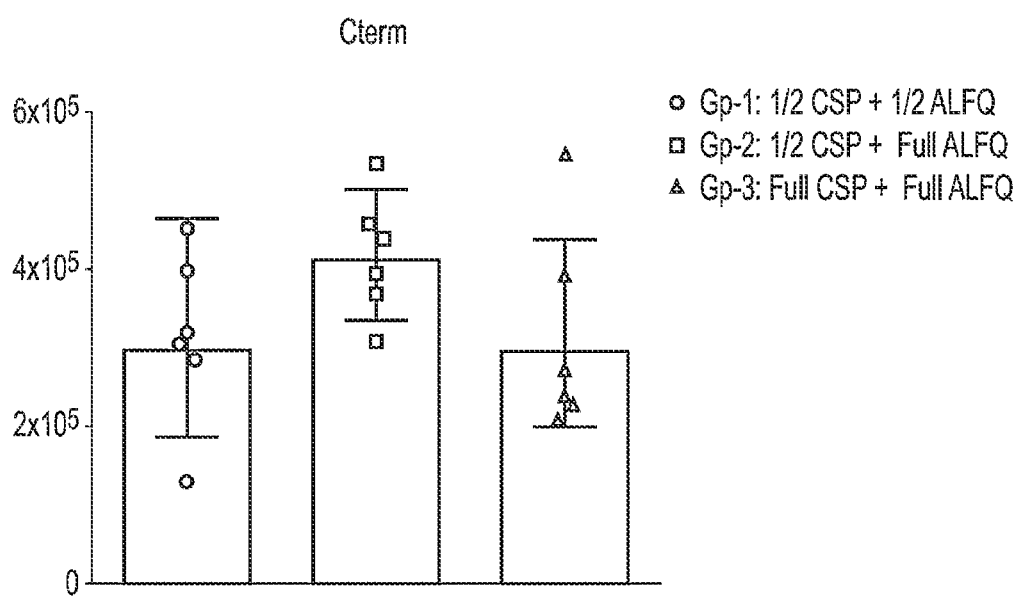
Figure 12E:
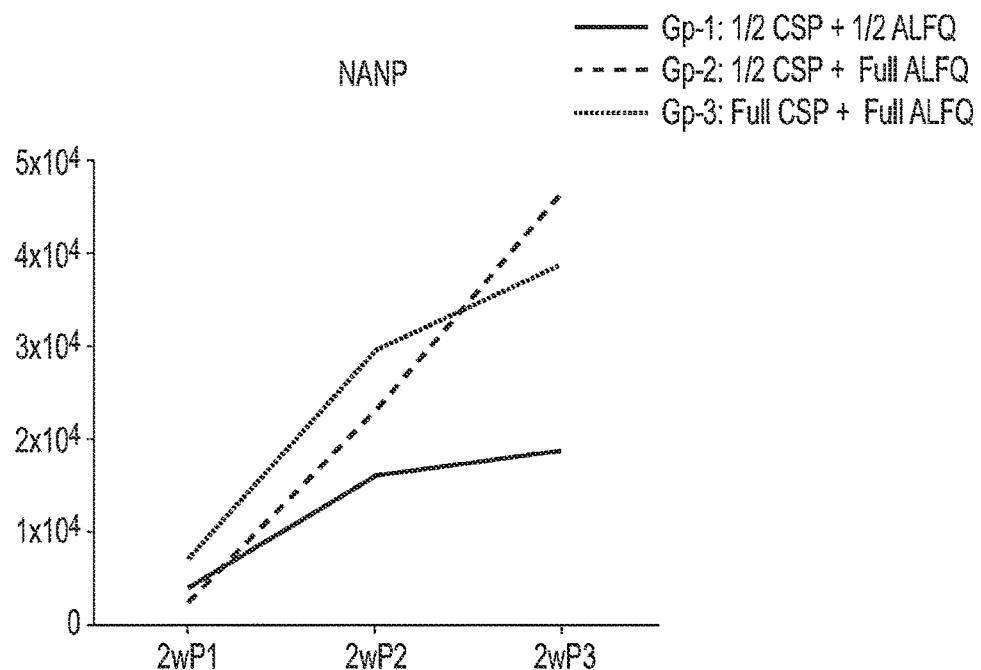
Figure 12F:
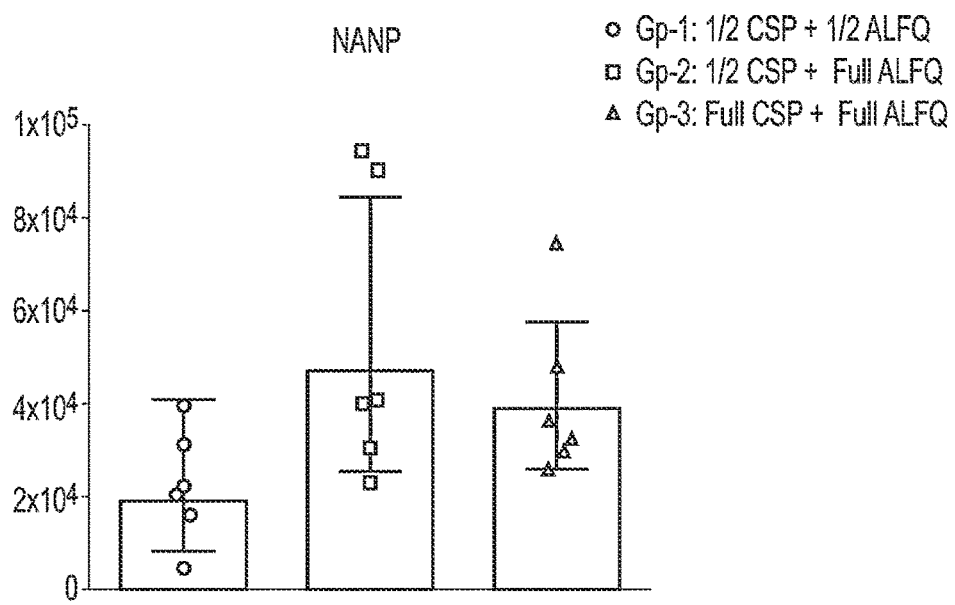

Hematological observations made on days 1, 3 and 7 post each vaccination (FIG. 11). All groups showed transient neutrophilic leukocytosis on day 1 post vaccination. In all groups, WBCs, neutrophils and monocyte counts day-1 post 1st and 2nd dose increased transiently and all three hematological parameters normalized by day 3. Eosinophils high most animals throughout the study (even before the first dose) probably due to an ongoing Strongyoides (whip worm) infection. RBC counts remained within the normal limits throughout the course of vaccination for all groups (FIG. 11).

Rhesus Immunogenicity

Figure 13:
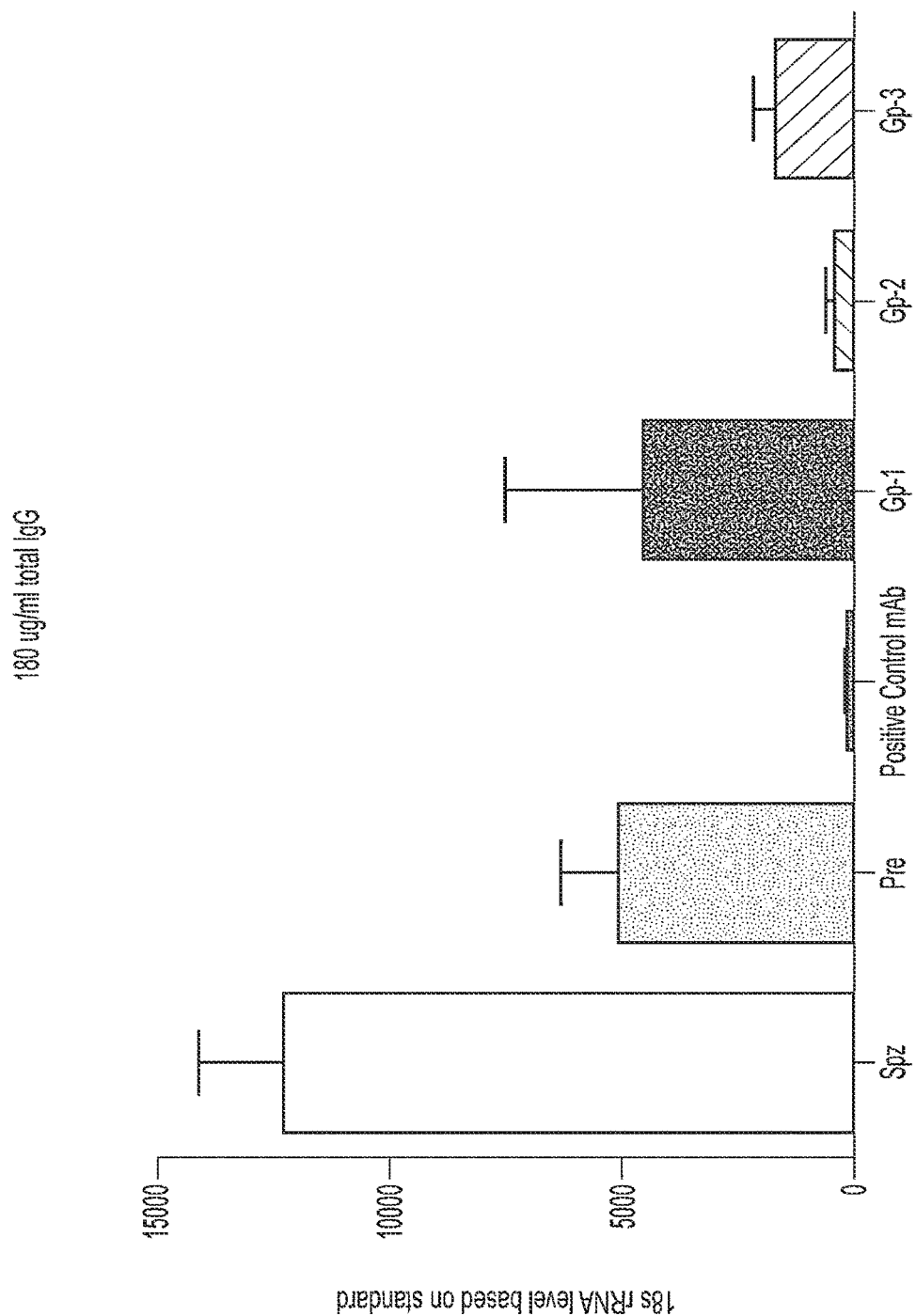
FIG. 13 depicts the results of an inhibition of liver stage dose assay in Rhesus monkeys using purified IgG from Groups-1, 3 and 3 total IgG. Parasite specific 18s rRNA was quantified against a standard with pre-immune (negative) and a CSP specific monoclonal antibody (positive) control.

ELISA against the full-length CSP antigen (FL) revealed 100% seroconversion all groups following the 1st dose (FIG. 12). While there was no statistically significant difference in antibody profiles between groups, the half dose adjuvant group-1 showed lower mean titer than the full-dose adjuvant groups-2 and -3 with respect to full-length, C-term and NANP titer. IgG produced from sera in each group was tested using in vitro inhibition of sporozoite development assay (ILSDA). Group-2 and Group-3 (both full dose adjuvant groups) showed significant inhibition of sporozoite development into human primary hepatic cells (FIG. 13). Thus FMP013 was immunogenic and antibodies were biologically active. A full dose of adjuvant was necessary for optimal response.

The invention claimed is:

1. A pharmaceutical composition comprising at least one antigen and an adjuvant composition, wherein the adjuvant composition comprises a saponin and a liposome comprising monophosphoryl lipid A (MPLA), cholesterol and a phospholipid that is in a liquid crystalline state at greater than or equal to 23° C., wherein the concentration of cholesterol to lipid in the liposome is greater than 50% (mol/mol), and wherein the antigen is soluble *Plasmodium falciparum* recombinant circumsporozoite protein (rCSP) comprising the amino acid sequence of SEQ ID NO:1, or a *P. falciparum* rCSP peptide that is at least 95% identical to the amino acid sequence of SEQ ID NO:1.

2. The pharmaceutical composition of claim 1, wherein the at least one saponin is QS7, QS18 or QS21 or mixtures thereof.

3. The pharmaceutical composition of claim 1, wherein the concentration of cholesterol to lipid in the liposome is at least about 50.1%, 50.2%, 50.3%, 50.4%, 50.5%, 50.6%, 50.7%, 50.8%, 50.9%, 51%, 52%, 53%, 54%, 55%, 56%, 57%, 58%, 59%, 60%, 61%, 62%, 63%, 64%, 65%, 66%, 67%, 68%, 69%, 70% or 71%.

4. The pharmaceutical composition of claim 3, wherein the phospholipid in the liposome is a phosphatidylcholine (PC) selected from the group consisting of dimyristoyl phosphatidylcholine (DMPC), dipalmitoyl phosphatidylcholine (DPPC) and distearyl phosphatidylcholine (DSPC).

5. The pharmaceutical composition of claim 4, wherein the liposome of the adjuvant composition further comprising a phosphatidylglycerol (PG) selected from dimyristoyl phosphatidylglycerol (DMPG), dipalmitoyl phosphatidylglycerol (DPPG) and distearyl phosphatidylglycerol (DSPG).

6. The pharmaceutical composition of claim 5, wherein the ratio of the PC to the PG (mol/mol) in the liposome is about 0.5:1, 1:1, 2:1, 3:1, 4:1, 5:1, 6:1, 7:1, 8:1, 9:1, 10:1, 11:1, 12:1, 13:1, 14:1, 15:1.

7. The pharmaceutical composition of claim 1, wherein the amount of MPLA is about 5 mg or less, about 4 mg or less, about 3 mg or less, about 2 mg or less, about 1 mg or less, about 0.9 mg or less, about 0.8 mg or less, about 0.7 mg or less, about 0.6 mg or less, about 0.5 mg or less, about 0.4 mg or less, about 0.3 mg or less, about 0.2 mg or less, about 0.1 mg or less, about 0.09 mg or less, about 0.08 mg or less, about 0.07 mg or less, about 0.06 mg or less, about 0.05 mg or less, about 0.04 mg or less, about 0.03 mg or less, about 0.02 mg or less or about 0.01 mg or less (total weight per ml liposome suspension).

8. The pharmaceutical composition of claim 1 where the liposome has a MPLA:phospholipid mole ratio of about 1:5.6 to about 1:880, or about 1:88 to about 1:220.

9. The pharmaceutical composition of claim 1, wherein the amount of saponin in the liposome is about 1 mg or less, about 0.9 mg or less, about 0.8 mg or less, about 0.7 mg or less, about 0.6 mg or less, about 0.5 mg or less, about 0.4 mg or less, about 0.3 mg or less, about 0.2 mg or less, about 0.1 mg or less, about 0.09 mg or less, about 0.08 mg or less, about 0.07 mg or less, about 0.06 mg or less, about 0.05 mg or less, about 0.04 mg or less, about 0.03 mg or less, about 0.02 mg or less, about 0.01 mg or less (total weight per ml liposome suspension).

10. The pharmaceutical composition of claim 1, wherein the liposome comprises multi-lamellar vesicles (MLV) of about 1 to about 4 µm in diameter or small uni-lamellar vesicles (SUV) of about 50 to about 100 nm in diameter.

11. The pharmaceutical composition of claim 1, further comprising a physiologically acceptable vehicle.

12. The pharmaceutical composition of claim 1, wherein the *P. falciparum* rCSP lacks $Met_1$ to $Cys_{25}$ of the N-terminal region of native *P. falciparum* circumsporozoite protein.

13. The pharmaceutical composition of claim 1, wherein the *P.falciparum* rCSP has 18 or 19 NANP (SEQ ID NO:13) repeats.

14. The pharmaceutical composition of claim 1, wherein the *P.falciparum* rCSP has 0 to 3 NVDP (SEQ ID NO:14) repeats.

15. The pharmaceutical composition of claim 1, wherein the *P.falciparum* rCSP has a C-terminal region that lacks ten to fourteen C-terminus amino acid residues of native *P. falciparum* circumsporozoite protein.

16. The pharmaceutical composition of claim 1, wherein the C-terminal residue of the *P.falciparum* rCSP is serine.

17. The pharmaceutical composition of claim 1, wherein the *P.falciparum* rCSP comprises the amino acid sequence of SEQ ID NO:8.

18. The pharmaceutical composition of claim 1, wherein the amount of the *P.falciparum* rCSP antigen is between about 0.01 µg and about 100 µg per dose or per administration.

19. The pharmaceutical composition of claim 1, wherein the amount of *P.falciparum* rCSP antigen is between about 1 µg to about 30 µg per dose per dose or administration.

20. The pharmaceutical composition of claim 1, wherein the adjuvant composition is in an amount from about 0.1 ml to about 10 ml.

21. A method of immunizing a subject against malaria, the method comprising administering a pharmaceutical composition to a subject at least once, wherein the pharmaceutical composition comprises at least one antigen and an adjuvant composition, wherein the adjuvant composition comprises a saponin and a liposome comprising monophosphoryl lipid A (MFLA), cholesterol and a phospholipid that is in a liquid crystalline state at greater than or equal to 23° C., wherein the concentration of cholesterol to lipid in the liposome is greater than 50% (mol/mol), and wherein the antigen is soluble *Plasmodium falciparum* recombinant circumsporozoite protein (rCSP) comprising the amino acid sequence of SEQ ID NO:1, or a *P. falciparum* rCSP peptide that is at least 95% identical to the amino acid sequence of SEQ ID NO:1.

22. The method of claim 21, wherein the pharmaceutical composition is administered to the subject more than once.

23. The method of claim 21, wherein the pharmaceutical composition is administered at least three times to the subject, with between 2-6 weeks in between each administration.

24. The method of claim 21, wherein the adjuvant composition is in an amount from about 0.1 ml to about 10 ml.

25. The method of claim 21, wherein the amount of *P.falciparum* rCSP antigen is between about 1 µg to about 30 µg per dose per dose or administration.

\* \* \* \* \*

```
                              SEQUENCE LISTING

<160> NUMBER OF SEQ ID NOS: 14

<210> SEQ ID NO 1
<211> LENGTH: 278
<212> TYPE: PRT
<213> ORGANISM: Artificial Sequence
<220> FEATURE:
<223> OTHER INFORMATION: recombinant Plasmodium Falciparum
      circumsporozoite polypeptide sequence

<400> SEQUENCE: 1

Tyr Gly Ser Ser Ser Asn Thr Arg Val Leu Asn Glu Leu Asn Tyr Asp
1               5                   10                  15

Asn Ala Gly Thr Asn Leu Tyr Asn Glu Leu Glu Met Asn Tyr Tyr Gly
            20                  25                  30

Lys Gln Glu Asn Trp Tyr Ser Leu Lys Lys Asn Ser Arg Ser Leu Gly
        35                  40                  45

Glu Asn Asp Asp Gly Asn Asn Glu Asp Asn Glu Lys Leu Arg Lys Pro
    50                  55                  60

Lys His Lys Lys Leu Lys Gln Pro Ala Asp Gly Asn Pro Asp Pro Asn
65                  70                  75                  80

Ala Asn Pro Asn Val Asp Pro Asn Ala Asn Pro Asn Val Asp Pro Asn
                85                  90                  95

Ala Asn Pro Asn Val Asp Pro Asn Ala Asn Pro Asn Ala Asn Pro Asn
            100                 105                 110

Ala Asn Pro Asn Ala Asn Pro Asn Ala Asn Pro Asn Ala Asn Pro Asn
        115                 120                 125

Ala Asn Pro Asn Ala Asn Pro Asn Ala Asn Pro Asn Ala Asn Pro Asn
    130                 135                 140

Ala Asn Pro Asn Ala Asn Pro Asn Ala Asn Pro Asn Ala Asn Pro Asn
145                 150                 155                 160

Ala Asn Pro Asn Ala Asn Pro Asn Lys Asn Asn Gln Gly Asn Gly Gln
                165                 170                 175

Gly His Asn Met Pro Asn Asp Pro Asn Arg Asn Val Asp Glu Asn Ala
            180                 185                 190

Asn Ala Asn Ser Ala Val Lys Asn Asn Asn Glu Glu Pro Ser Asp
        195                 200                 205

Lys His Ile Lys Glu Tyr Leu Asn Lys Ile Gln Asn Ser Leu Ser Thr
    210                 215                 220

Glu Trp Ser Pro Cys Ser Val Thr Cys Gly Asn Gly Ile Gln Val Arg
225                 230                 235                 240

Ile Lys Pro Gly Ser Ala Asn Lys Pro Lys Asp Glu Leu Asp Tyr Ala
                245                 250                 255

Asn Asp Ile Glu Lys Lys Ile Cys Lys Met Glu Lys Cys Ser Ser Val
            260                 265                 270

Phe Asn Val Val Asn Ser
        275

<210> SEQ ID NO 2
<211> LENGTH: 834
<212> TYPE: DNA
<213> ORGANISM: Artificial Sequence
<220> FEATURE:
```

-continued

<223> OTHER INFORMATION: recombinant Plasmodium Falciparum circumsporozoite protein nucleic acid sequence

<400> SEQUENCE: 2

```
tacggctctt cttctaacac tcgcgtgctg aatgaactga attacgataa cgctggcacc     60
aacctgtata atgaactgga aatgaactat tacggtaagc aggaaaactg gtatagcctg    120
aaaaagaaca gccgcagcct gggtgaaaac gacgacggta acaacgagga caatgaaaaa    180
ctgcgcaagc ctaaacacaa aaagctgaaa cagccggcgg acggtaatcc ggatccaaac    240
gcaaacccga atgtggatcc gaacgccaat ccgaacgtgg acccgaacgc gaacccaaac    300
gttgatccta acgccaaccc gaacgctaac cctaacgcca acccaaacgc aaaccctaat    360
gctaacccaa acgcgaaccc gaacgcaaat ccgaacgcga accctaacgc taaccctaac    420
gcaaacccta acgcaaaccc aaacgccaac cctaacgcga acccgaatgc gaatccgaac    480
gctaatccaa atgctaaccc gaacaaaaac aaccagggca acggccaggg tcacaatatg    540
ccgaacgatc cgaatcgcaa cgtggacgaa aatgctaatg ctaacagcgc agtgaaaaac    600
aataataacg aggagccgag cgataagcac atcaaagaat atctgaacaa gatccagaat    660
agcctgtcca ccgaatggag cccgtgctct gtcacgtgcg gtaacggcat tcaagttcgt    720
atcaaaccag gtagcgccaa caagccgaaa gacgaactgg actacgcaaa cgacattgag    780
aaaaagatct gtaaaatgga aaaatgcagc tctgtcttta acgtcgttaa ctcc          834
```

<210> SEQ ID NO 3
<211> LENGTH: 33
<212> TYPE: DNA
<213> ORGANISM: Escherichia coli
<220> FEATURE:
<221> NAME/KEY: misc_feature
<223> OTHER INFORMATION: E. coli derived N terminal 6X-His tag nucleotide sequence derived from E. coli vector

<400> SEQUENCE: 3

```
atggcacacc atcatcatca tcatcccggg atg                                  33
```

<210> SEQ ID NO 4
<211> LENGTH: 36
<212> TYPE: DNA
<213> ORGANISM: Escherichia coli
<220> FEATURE:
<221> NAME/KEY: misc_feature
<223> OTHER INFORMATION: E. Coli derived C-terminal 6XHIS tag nucleotide sequence derived from E. coli vector

<400> SEQUENCE: 4

```
ggcggccgcc tcgagcacca ccaccaccac cactga                               36
```

<210> SEQ ID NO 5
<211> LENGTH: 902
<212> TYPE: DNA
<213> ORGANISM: Artificial Sequence
<220> FEATURE:
<223> OTHER INFORMATION: rCS/D; recombinant Plasmodium Falciparum circumsporozoite protein nucleic acid sequence with 19 NANP repeats and 3 NVDP repeats, and including N and C terminal 6X HIS tags

<400> SEQUENCE: 5

```
atggcacacc atcatcatca tcatcccggg atgtacggct cttcttctaa cactcgcgtg     60
ctgaatgaac tgaattacga taacgctggc accaacctgt ataatgaact ggaaatgaac    120
tattacggta agcaggaaaa ctggtatagc ctgaaaaaga acagccgcag cctgggtgaa    180
```

```
aacgacgacg gtaacaacga ggacaatgaa aaactgcgca agcctaaaca caaaaagctg    240
aaacagccgg cggacggtaa tccggatcca acgcaaacc cgaatgtgga tccgaacgca    300
atccgaacgt ggacccgaac gcgaacccaa acgttgatcc taacgccaac ccgaacgcta    360
accctaacgc caacccaaac gcaaacccta atgctaaccc aaacgcgaac ccgaacgcaa    420
atccgaacgc gaaccctaac gctaacccta acgcaaaccc taacgcaaac ccaaacgcca    480
accctaacgc gaacccgaat gcgaatccga acgctaatcc aaatgctaac ccgaacaaaa    540
acaaccaggg caacggccag ggtcacaata tgccgaacga tccgaatcgc aacgtggacg    600
aaaatgctaa tgctaacagc gcagtgaaaa acaataataa cgaggagccg agcgataagc    660
acatcaaaga atatctgaac aagatccaga atagcctgtc caccgaatgg agcccgtgct    720
ctgtcacgtg cggtaacggc attcaagttc gtatcaaacc aggtagcgcc aacaagccga    780
aagacgaact ggactacgca acgacattg agaaaaagat ctgtaaaatg gaaaaatgca    840
gctctgtctt taacgtcgtt aactccggcg ccgcctcga gcaccaccac caccaccact    900
ga                                                                  902
```

```
<210> SEQ ID NO 6
<211> LENGTH: 11
<212> TYPE: PRT
<213> ORGANISM: Escherichia coli
<220> FEATURE:
<221> NAME/KEY: MISC_FEATURE
<223> OTHER INFORMATION: N-terminal 6X HIS tag polypeptide sequence
      derived from E. coli vector

<400> SEQUENCE: 6

Met Ala His His His His His His Pro Gly Met
1               5                   10

<210> SEQ ID NO 7
<211> LENGTH: 11
<212> TYPE: PRT
<213> ORGANISM: Escherichia coli
<220> FEATURE:
<221> NAME/KEY: MISC_FEATURE
<223> OTHER INFORMATION: C-terminal 6X HIS tag polypeptide sequence
      derived from E. coli vector

<400> SEQUENCE: 7

Gly Gly Arg Leu Glu His His His His His His
1               5                   10

<210> SEQ ID NO 8
<211> LENGTH: 300
<212> TYPE: PRT
<213> ORGANISM: Artificial Sequence
<220> FEATURE:
<223> OTHER INFORMATION: rCS/D; recombinant Plasmodium Falciparum
      circumsporozoite polypeptide sequence including an N- and
      C-terminal E. Coli derived 6X HIS tags and Tyr26 start amino acid
      of CSP

<400> SEQUENCE: 8

Met Ala His His His His His His Pro Gly Met Tyr Gly Ser Ser Ser
1               5                   10                  15

Asn Thr Arg Val Leu Asn Glu Leu Asn Tyr Asp Asn Ala Gly Thr Asn
            20                  25                  30

Leu Tyr Asn Glu Leu Glu Met Asn Tyr Tyr Gly Lys Gln Glu Asn Trp
        35                  40                  45
```

```
Tyr Ser Leu Lys Lys Asn Ser Arg Ser Leu Gly Glu Asn Asp Asp Gly
     50                  55                  60

Asn Asn Glu Asp Asn Glu Lys Leu Arg Lys Pro Lys His Lys Lys Leu
 65                  70                  75                  80

Lys Gln Pro Ala Asp Gly Asn Pro Asp Pro Asn Ala Asn Pro Asn Val
                 85                  90                  95

Asp Pro Asn Ala Asn Pro Asn Val Asp Pro Asn Ala Asn Pro Asn Val
                100                 105                 110

Asp Pro Asn Ala Asn Pro Asn Ala Asn Pro Asn Ala Asn Pro Asn Ala
                115                 120                 125

Asn Pro Asn Ala Asn Pro Asn Ala Asn Pro Asn Ala Asn Pro Asn Ala
130                 135                 140

Asn Pro Asn Ala Asn Pro Asn Ala Asn Pro Asn Ala Asn Pro Asn Ala
145                 150                 155                 160

Asn Pro Asn Ala Asn Pro Asn Ala Asn Pro Asn Ala Asn Pro Asn Ala
                165                 170                 175

Asn Pro Asn Lys Asn Asn Gln Gly Asn Gly Gln Gly His Asn Met Pro
                180                 185                 190

Asn Asp Pro Asn Arg Asn Val Asp Glu Asn Ala Asn Ala Asn Ser Ala
                195                 200                 205

Val Lys Asn Asn Asn Glu Glu Pro Ser Asp Lys His Ile Lys Glu
210                 215                 220

Tyr Leu Asn Lys Ile Gln Asn Ser Leu Ser Thr Glu Trp Ser Pro Cys
225                 230                 235                 240

Ser Val Thr Cys Gly Asn Gly Ile Gln Val Arg Ile Lys Pro Gly Ser
                245                 250                 255

Ala Asn Lys Pro Lys Asp Glu Leu Asp Tyr Ala Asn Asp Ile Glu Lys
                260                 265                 270

Lys Ile Cys Lys Met Glu Lys Cys Ser Ser Val Phe Asn Val Val Asn
                275                 280                 285

Ser Gly Gly Arg Leu Glu His His His His His His
290                 295                 300

<210> SEQ ID NO 9
<211> LENGTH: 281
<212> TYPE: PRT
<213> ORGANISM: Artificial Sequence
<220> FEATURE:
<223> OTHER INFORMATION: rCS/A- recombinant Plasmodium Falciparum
      circumsporozoite polypeptide sequence with 18 NANP repeats and
      Gln21 starting amino acid and an N-terminal 6X HIS tag

<400> SEQUENCE: 9

Met Ala His His His His His His Pro Gly Gly Ser Gln Glu Tyr Gln
 1               5                  10                  15

Cys Tyr Gly Ser Ser Asn Thr Arg Val Leu Asn Glu Leu Asn Tyr
                 20                  25                  30

Asp Asn Ala Gly Thr Asn Leu Tyr Asn Glu Leu Glu Met Asn Tyr Tyr
                 35                  40                  45

Gly Lys Gln Glu Asn Trp Tyr Ser Leu Lys Lys Asn Ser Arg Ser Leu
 50                  55                  60

Gly Glu Asn Asp Asp Gly Asn Asn Glu Asp Asn Glu Lys Leu Arg Lys
 65                  70                  75                  80

Pro Lys His Lys Lys Leu Lys Gln Pro Ala Asp Gly Asn Pro Asn Ala
                 85                  90                  95

Asn Pro Asn Ala Asn Pro Asn Ala Asn Pro Asn Ala Asn Pro Asn Ala
```

```
                        100                 105                 110
Asn Pro Asn Ala Asn Pro Asn Ala Asn Pro Asn Ala Asn Pro Asn Ala
            115                 120                 125
Asn Pro Asn Ala Asn Pro Asn Ala Asn Pro Asn Ala Asn Pro Asn Ala
            130                 135                 140
Asn Pro Asn Ala Asn Pro Asn Ala Asn Pro Asn Ala Asn Pro Asn Ala
145                 150                 155                 160
Asn Pro Asn Ala Asn Pro Asn Lys Asn Asn Gln Gly Asn Gly Gln Gly
            165                 170                 175
His Asn Met Pro Asn Asp Pro Asn Arg Asn Val Asp Glu Asn Ala Asn
            180                 185                 190
Ala Asn Ser Ala Val Lys Asn Asn Asn Glu Glu Pro Ser Asp Lys
            195                 200                 205
His Ile Lys Glu Tyr Leu Asn Lys Ile Gln Asn Ser Leu Ser Thr Glu
            210                 215                 220
Trp Ser Pro Cys Ser Val Thr Cys Gly Asn Gly Ile Gln Val Arg Ile
225                 230                 235                 240
Lys Pro Gly Ser Ala Asn Lys Pro Lys Asp Glu Leu Asp Tyr Ala Asn
            245                 250                 255
Asp Ile Glu Lys Lys Ile Cys Lys Met Glu Lys Cys Ser Ser Val Phe
            260                 265                 270
Asn Val Val Asn Ser Ser Ile Gly Leu
            275                 280

<210> SEQ ID NO 10
<211> LENGTH: 276
<212> TYPE: PRT
<213> ORGANISM: Artificial Sequence
<220> FEATURE:
<223> OTHER INFORMATION: rCS/B- recombinant Plasmodium Falciparum
      circumsporozoite polypeptide sequence with 18 NANP repeats and
      Tyr26 start amino acid and an N-terminal 6X HIS tag

<400> SEQUENCE: 10

Met Ala His His His His His His Pro Gly Gly Ser Tyr Gly Ser Ser
1               5                   10                  15
Ser Asn Thr Arg Val Leu Asn Glu Leu Asn Tyr Asp Asn Ala Gly Thr
            20                  25                  30
Asn Leu Tyr Asn Glu Leu Glu Met Asn Tyr Tyr Gly Lys Gln Glu Asn
            35                  40                  45
Trp Tyr Ser Leu Lys Lys Asn Ser Arg Ser Leu Gly Glu Asn Asp Asp
            50                  55                  60
Gly Asn Asn Glu Asp Asn Glu Lys Leu Arg Lys Pro Lys His Lys Lys
65                  70                  75                  80
Leu Lys Gln Pro Ala Asp Gly Asn Pro Asn Ala Asn Pro Asn Ala Asn
            85                  90                  95
Pro Asn Ala Asn Pro Asn Ala Asn Pro Asn Ala Asn Pro Asn Ala Asn
            100                 105                 110
Pro Asn Ala Asn Pro Asn Ala Asn Pro Asn Ala Asn Pro Asn Ala Asn
            115                 120                 125
Pro Asn Ala Asn Pro Asn Ala Asn Pro Asn Ala Asn Pro Asn Ala Asn
            130                 135                 140
Pro Asn Ala Asn Pro Asn Ala Asn Pro Asn Ala Asn Pro Asn Ala Asn
145                 150                 155                 160
Pro Asn Lys Asn Asn Gln Gly Asn Gly Gln Gly His Asn Met Pro Asn
            165                 170                 175
```

Asp Pro Asn Arg Asn Val Asp Glu Asn Ala Asn Ala Asn Ser Ala Val
            180                 185                 190

Lys Asn Asn Asn Glu Glu Pro Ser Asp Lys His Ile Lys Glu Tyr
        195                 200                 205

Leu Asn Lys Ile Gln Asn Ser Leu Ser Thr Glu Trp Ser Pro Cys Ser
    210                 215                 220

Val Thr Cys Gly Asn Gly Ile Gln Val Arg Ile Lys Pro Gly Ser Ala
225                 230                 235                 240

Asn Lys Pro Lys Asp Glu Leu Asp Tyr Ala Asn Asp Ile Glu Lys Lys
                245                 250                 255

Ile Cys Lys Met Glu Lys Cys Ser Ser Val Phe Asn Val Val Asn Ser
            260                 265                 270

Ser Ile Gly Leu
        275

<210> SEQ ID NO 11
<211> LENGTH: 228
<212> TYPE: PRT
<213> ORGANISM: Artificial Sequence
<220> FEATURE:
<223> OTHER INFORMATION: rCS/C- recombinant Plasmodium Falciparum
      circumsporozoite polypeptide with 5 NANP repeats and 2 NVDP
      repeats and Tyr26 start amino acid and a N-terminal 6X HIS tag
      sequence

<400> SEQUENCE: 11

Met Ala His His His His His His Pro Gly Tyr Gly Ser Ser Asn
1               5                   10                  15

Thr Arg Val Leu Asn Glu Leu Asn Tyr Asp Asn Ala Gly Thr Asn Leu
            20                  25                  30

Tyr Asn Glu Leu Glu Met Asn Tyr Tyr Gly Lys Gln Glu Asn Trp Tyr
        35                  40                  45

Ser Leu Lys Lys Asn Ser Arg Ser Leu Gly Glu Asn Asp Asp Gly Asn
    50                  55                  60

Asn Glu Asp Asn Glu Lys Leu Arg Lys Pro Lys His Lys Lys Leu Lys
65                  70                  75                  80

Gln Pro Ala Asp Gly Asn Pro Asp Pro Asn Ala Asn Pro Asn Val Asp
                85                  90                  95

Pro Asn Ala Asn Pro Asn Val Asp Pro Asn Ala Asn Pro Asn Ala Asn
            100                 105                 110

Pro Asn Ala Asn Pro Asn Lys Asn Asn Gln Gly Asn Gly Gln Gly His
        115                 120                 125

Asn Met Pro Asn Asp Pro Asn Arg Asn Val Asp Glu Asn Ala Asn Ala
    130                 135                 140

Asn Ser Ala Gly Lys Asn Asn Asn Glu Glu Pro Ser Asp Lys His
145                 150                 155                 160

Ile Lys Glu Tyr Leu Asn Lys Ile Gln Asn Ser Leu Ser Thr Glu Trp
                165                 170                 175

Ser Pro Cys Ser Val Thr Cys Gly Asn Gly Ile Gln Val Arg Ile Lys
            180                 185                 190

Pro Gly Ser Ala Asn Lys Pro Lys Asp Glu Leu Asp Tyr Ala Asn Asp
        195                 200                 205

Ile Glu Lys Lys Ile Cys Lys Met Glu Lys Cys Ser Ser Val Phe Asn
    210                 215                 220

Val Val Asn Ser
225

<210> SEQ ID NO 12
<211> LENGTH: 369
<212> TYPE: PRT
<213> ORGANISM: Artificial Sequence
<220> FEATURE:
<223> OTHER INFORMATION: rCS/E- recombinant Plasmodium Falciparum
circumsporozoite polypeptide with 38 NANP repeats and 4 NVDP
repeats and Tyr26 start amino acid and a N-terminal 6X HIS tag sequence

<400> SEQUENCE: 12

```
Met Ala His His His His His His Pro Gly Met Tyr Gly Ser Ser Ser
1               5                   10                  15

Asn Thr Arg Val Leu Asn Glu Leu Asn Tyr Asp Asn Ala Gly Thr Asn
            20                  25                  30

Leu Tyr Asn Glu Leu Glu Met Asn Tyr Tyr Gly Lys Gln Glu Asn Trp
        35                  40                  45

Tyr Ser Leu Lys Lys Asn Ser Arg Ser Leu Gly Glu Asn Asp Asp Gly
    50                  55                  60

Asn Asn Glu Asp Asn Glu Lys Leu Arg Lys Pro Lys His Lys Lys Leu
65                  70                  75                  80

Lys Gln Pro Ala Asp Gly Asn Pro Asp Pro Asn Ala Asn Pro Asn Val
                85                  90                  95

Asp Pro Asn Ala Asn Pro Asn Val Asp Pro Asn Ala Asn Pro Asn Val
            100                 105                 110

Asp Pro Asn Ala Asn Pro Asn Ala Asn Pro Asn Ala Asn Pro Asn Ala
        115                 120                 125

Asn Pro Asn Ala Asn Pro Asn Ala Asn Pro Asn Ala Asn Pro Asn Ala
    130                 135                 140

Asn Pro Asn Ala Asn Pro Asn Ala Asn Pro Asn Ala Asn Pro Asn Ala
145                 150                 155                 160

Asn Pro Asn Ala Asn Pro Asn Ala Asn Pro Asn Ala Asn Pro Asn Ala
                165                 170                 175

Asn Pro Asn Ala Asn Pro Asn Val Asp Pro Asn Ala Asn Pro Asn Ala
            180                 185                 190

Asn Pro Asn Ala Asn Pro Asn Ala Asn Pro Asn Ala Asn Pro Asn Ala
        195                 200                 205

Asn Pro Asn Ala Asn Pro Asn Ala Asn Pro Asn Ala Asn Pro Asn Ala
    210                 215                 220

Asn Pro Asn Ala Asn Pro Asn Ala Asn Pro Asn Ala Asn Pro Asn Ala
225                 230                 235                 240

Asn Pro Asn Ala Asn Pro Asn Ala Asn Pro Asn Ala Asn Pro Asn Ala
                245                 250                 255

Asn Pro Asn Lys Asn Asn Gln Gly Asn Gly Gln Gly His Asn Met Pro
            260                 265                 270

Asn Asp Pro Asn Arg Asn Val Asp Glu Asn Ala Asn Ala Asn Ser Ala
        275                 280                 285

Val Lys Asn Asn Asn Asn Glu Glu Pro Ser Asp Lys His Ile Lys Glu
    290                 295                 300

Tyr Leu Asn Lys Ile Gln Asn Ser Leu Ser Thr Glu Trp Ser Pro Cys
305                 310                 315                 320

Ser Val Thr Cys Gly Asn Gly Ile Gln Val Arg Ile Lys Pro Gly Ser
                325                 330                 335

Ala Asn Lys Pro Lys Asp Glu Leu Asp Tyr Ala Asn Asp Ile Glu Lys
            340                 345                 350
```

```
Lys Ile Cys Lys Met Glu Lys Cys Ser Ser Val Phe Asn Val Val Asn
        355                 360                 365

Ser

<210> SEQ ID NO 13
<211> LENGTH: 4
<212> TYPE: PRT
<213> ORGANISM: Artificial Sequence
<220> FEATURE:
<223> OTHER INFORMATION: Repeat sequence derived from P. falciparum CSP

<400> SEQUENCE: 13

Asn Ala Asn Pro
1

<210> SEQ ID NO 14
<211> LENGTH: 4
<212> TYPE: PRT
<213> ORGANISM: Artificial Sequence
<220> FEATURE:
<223> OTHER INFORMATION: Repeat sequence derived from P. falciparum CSP

<400> SEQUENCE: 14

Asn Val Asp Pro
1
```

UNITED STATES PATENT AND TRADEMARK OFFICE
CERTIFICATE OF CORRECTION

| | | |
|---|---|---|
| PATENT NO. | : 11,583,578 B2 | Page 1 of 1 |
| APPLICATION NO. | : 16/607917 | |
| DATED | : February 21, 2023 | |
| INVENTOR(S) | : Sheetij Dutta et al. | |

It is certified that error appears in the above-identified patent and that said Letters Patent is hereby corrected as shown below:

On the Title Page

Item (54) and in the Specification Column 1 Line 2, the Title, please delete "RECOMBINANR XIEXUMAPOEOZOITE" and insert --RECOMBINANT CIRCUMSPOROZOITE--

Signed and Sealed this
Twenty-fifth Day of April, 2023

Katherine Kelly Vidal
*Director of the United States Patent and Trademark Office*